United States Patent
Wang et al.

(10) Patent No.: US 11,668,710 B2
(45) Date of Patent: Jun. 6, 2023

(54) ASSAYS FOR THE DETECTION OF A BLOCKING ANALYTE

(71) Applicant: NOVODIAX, INC., Hayward, CA (US)

(72) Inventors: Jianfu Wang, Union City, CA (US);
Nan Zhang, Pleasanton, CA (US);
Shuo Chen, Milpitas, CA (US); Jin Vale Wu, Union City, CA (US)

(73) Assignee: NOVODIAX, INC., Hayward, CA (US)

( * ) Notice: Subject to any disclaimer, the term of this patent is extended or adjusted under 35 U.S.C. 154(b) by 14 days.

(21) Appl. No.: 17/325,681

(22) Filed: May 20, 2021

(65) Prior Publication Data

US 2021/0364508 A1    Nov. 25, 2021

Related U.S. Application Data

(60) Provisional application No. 63/124,579, filed on Dec. 11, 2020, provisional application No. 63/029,243, filed on May 22, 2020.

(51) Int. Cl.
| | |
|---|---|
| *G01N 33/543* | (2006.01) |
| *G01N 33/68* | (2006.01) |
| *B01L 3/00* | (2006.01) |
| *G01N 33/58* | (2006.01) |

(52) U.S. Cl.
CPC ...... *G01N 33/54387* (2021.08); *B01L 3/5023* (2013.01); *G01N 33/54306* (2013.01); *G01N 33/54388* (2021.08); *G01N 33/581* (2013.01); *G01N 33/585* (2013.01); *G01N 33/6842* (2013.01); *G01N 33/6854* (2013.01); *B01L 2300/0825* (2013.01); *B01L 2400/0406* (2013.01)

(58) Field of Classification Search
CPC ....... G01N 33/54387; G01N 33/54388; G01N 33/581; G01N 33/585; G01N 33/6842; G01N 33/6854
See application file for complete search history.

(56) References Cited

PUBLICATIONS

EPIGENTEK. SeroFlash SARS-CoV-2 Neutralizing Antibody Assay Fast Kit (May 20, 2020).*
Yang et al. A rapid immunochromatographic strip for neutralizing antibodies detection of foot and mouth disease virus serotype O. RSC Adv. 7: 48095-48101 (2017).*
Ngom et al. Development and application of lateral flow strip technology for detection of infectious agents and chemical contaminants: a review. Anal. Bioanal. Chem. 397: 1113-1135 (2010).*

(Continued)

*Primary Examiner* — Gailene Gabel
(74) *Attorney, Agent, or Firm* — Ping Wang; Rimon Law

(57) ABSTRACT

The present disclosure provides assays, such as lateral flow assays, and components thereof for detection of an analyte, e.g., a neutralizing antibody, that blocks binding of a first molecular component and a second molecular component of a molecular binding pair. In some embodiments, the disclosed assays and components thereof enable the rapid detection of a SARS-CoV-2 neutralizing antibody in a sample from an individual. Also provided in other aspects of the disclosure are devices, methods of making and using, and kits of the assays described herein.

6 Claims, 10 Drawing Sheets

(56) References Cited

PUBLICATIONS

Li et al. Development and clinical application of a rapid IgM-IgG combined antibody test for SARS-COV-2 Infection disease. J. Med. Virol. 92: 1518-1524 (Apr. 13, 2020).*

Tan Chee Wah et al: "A SARS-CoV-2 surrogate virus neutralization test (sVNT) based on antibody-mediated blockage of ACE2-spike (RBD) protein-protein interaction", Research Square, 2020, pp. 1-15.

Zhengtu Li et al: "Development and clinical application of a rapid IgM-IgG combined antibody test for SARS-CoV-2 infection diagnosis", Journal of Medical Virology, vol. 92(9), 2020, pp. 1518-1524.

Khan Saahir et al: "Analysis of Serologic Cross-Reactivity Between Common Human Coronaviruses and SARS-CoV-2 Using Coronavirus Antigen Microarray", bioRxiv : the preprint server for biology, 2020.

Shanghai Lei et al: "Neutralization of SARS-CoV-2 spike pseudotyped virus by recombinant ACE2-lg", Nature Communications, 2020, pp. 2070.

"Application Note Pro-Detect Rapid assays", , Sep. 18, 2018 (Sep. 18, 2018), XP055839243, URL:https://assets.thermofisher.com/TFS-Assets/BID/Application-Notes/ rapid-sensitive-determination-recombinant-protein-expression-app-note.pdf.

Zhang Nan et al: "A lateral flow test detecting SARS-CoV-2 neutralizing antibodies", medRxiv, 2020.

Lake Douglas F. et al: "Development of a Rapid Point-Of-Care Test that Measures Neutralizing Antibodies to SARS-CoV-2", medRxiv, 2020.

International Search Report and Written Opinion of the International Searching Authority of International application No. PCT/US2021/070586 dated Sep. 20, 2021.

\* cited by examiner

| Neutralizing analyte in sample | First test line (208) | Control line (210) |
|---|---|---|
| + | - | + |
| - | + | + |

| Neutralizing analyte in sample | First test line (308) | Control line (310) |
|---|---|---|
| + | − | + |
| − | + | + |

| SARS-CoV-2 specific Abs in sample | 1st test line (T1) | 2nd test line (T2) | 3rd test line (T3) | Control line (C) |
|---|---|---|---|---|
| IgG+, IgM+, NAbs+ | Vary | + | + | + |
| IgG+, IgM-, NAbs+ | Vary | + | - | + |
| IgG-, IgM+, NAbs+ | Vary | - | + | + |
| IgG-, IgM-, NAbs- | + | - | - | + |

ASSAYS FOR THE DETECTION OF A BLOCKING ANALYTE

RELATED APPLICATIONS

This application claims priority from U.S. Provisional Application Ser. No. 63/029,243, filed May 22, 2020, and U.S. Provisional Application Ser. No. 63/124,579, filed on Dec. 11, 2020. The entirety of the aforementioned applications is incorporated herein by reference.

FIELD

The present disclosure is directed to assays for detection of an analyte, such as a neutralizing antibody, that blocks binding of a first molecular component and a second molecular component of a molecular binding pair. Also provided in other aspects of the disclosure are devices, methods of making and using, and kits of the assays described herein.

BACKGROUND

Point-of-care assays are generally designed to detect an analyte based on a structural feature of that analyte. An example of such an assay is a lateral flow immunoassay. Lateral flow immunoassays are widely used as point-of-care tests across multiple industry sectors, including healthcare diagnostics, disease diagnostics, environmental testing, animal health testing, and food and feed testing. Most lateral flow assays use immobilized antibodies as the capturing agents, which recognize a unique structure (e.g., an epitope) of the target molecule. Such a structure-based recognition often results in unsatisfactory sensitivity and/or specificity in clinical applications. Therefore, there exist a need for point-of-care assays with better sensitivity and specificity.

SUMMARY

One aspect of the present application relates to a test strip for detection of a neutralizing antibody that blocks binding of a first molecular component and a second molecular component of a molecular binding pair. In some embodiments, the test strip comprises (a) a chromatographic strip having a first end region and a second end region, wherein the chromatographic strip comprises a first test zone and wherein the first molecular component is immobilized within the first test zone; and (b) a sample binding zone comprising a binding pad having a first end region and a second end region, wherein the binding pad comprises the second molecular component labeled with a detection agent, wherein the first end region of the chromatographic strip is in direct fluid flow communication with the second end region of the binding pad, and wherein (1) the first molecular component comprises a viral surface polypeptide or a fragment thereof and the second molecular component comprises a cell-surface polypeptide or a fragment thereof, or (2) the first molecular component comprises the cell-surface polypeptide or a fragment thereof and the second component comprises the viral surface polypeptide or a fragment thereof.

Another aspect of the present application relates to a method of detecting the presence or absence of a neutralizing antibody that blocks binding of a first molecular component and a second molecular component of a molecular binding pair, the method comprising: (a) introducing a sample from an individual to the test strip of the present application; and (b) analyzing one or more read-outs of the test strip, wherein an absence of detectable binding in the first test zone indicates the presence of the neutralizing antibody in the sample, and a presence of detectable binding in the first test zone indicates the absence of the neutralizing antibody in the sample.

Another aspect of the present application relates to a device comprising the test strip of the present application.

Another aspect of the present application relates to a test kit. In some embodiments, the test kit comprises the test strip of the present application and a sample collection device.

Figure 1:
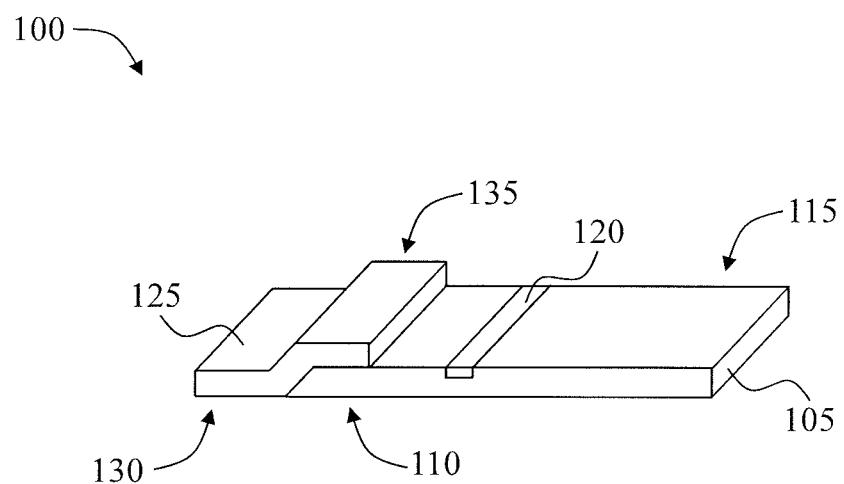
FIG. 1 shows a schematic of an exemplary test strip 100 having a test zone 120.

While the present disclosure will now be described in detail, and it is done so in connection with the illustrative embodiments, it is not limited by the particular embodiments illustrated in the figures and the appended claims.

DETAILED DESCRIPTION

The present application provides, in some aspects, assays for detection of an analyte, such as a neutralizing antibody, that blocks binding of molecular components of a molecular binding system. The present disclosure is based, at least in part, on the inventor's unique perspective and results demonstrating that simple and rapid assays can be designed and run to rapidly (such as in 15 minutes or less) detect an analyte based on a functional attribute of the analyte, e.g., an interaction-blocking characteristic. The assay system of the present application utilizes non-antibody molecules with high binding affinity to their binding counterpart for the development of a competitive form of lateral flow assay. A fundamental difference of such competitive lateral flow assay from the classical competitive later flow assay is the detection of a function rather than the detection of a molecule. Assays can thus be designed using at least a first and second molecular component of a molecular binding system, such as a molecular binding pair, to interrogate a sample for an analyte that blocks interaction and/or association of the molecular binding system. Such assays can further comprise features for further characterizing the analyte. For example, in the case of an analyte being a neutralizing antibody, the assay can be designed to characterize the antibody, e.g., determine the Ig class of the neutralizing antibody. The assays disclosed herein have broad applicability and can be used as a point-of-care assay.

The device of the present application is particularly useful for rapid detection of a virus-neutralizing antibody, such an antibody that neutralizes cell entry pathways for the SARS-CoV-2 coronavirus. In a battle with a virus outbreak, such as the current COVID-19 pandemic, such assays are capable of rapidly providing vital information to understand how many people have obtained immunity through disease, asymptomatic infection, or even explosion to cross-reactive antigen of another pathogen. Current virus neutralization assays require cell culture and use of live viruses, therefore is difficult to implement such tests for large scale epidemic or population surveys. The assays described herein, such as lateral flow or ELISA assays, overcome the current limitations of these known assays and provide rapid, convenient, and point-of-care testing capabilities.

Thus, in some aspects, provided herein is an assay for detection of an analyte, such as a neutralizing antibody, that blocks binding of a first molecular component and a second molecular component of a molecular binding pair. Lateral flow assays are described in detail, however, this description is not meant to limit the teachings of the assay formats to only lateral flow assays. One of ordinary skill in the art will readily recognize that the assay formats taught herein can be applied to other assay formats, such as ELISA.

In other aspects, also provided are devices, methods of making and using, and kits of the assays described herein. All references cited herein, including patent applications and publications, are incorporated by reference in their entirety.

I. Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-translational modifications of the polypeptide, for example, glycosylation, sialylation, acetylation, phosphorylation, and the like.

The term "antibody" includes full-length antibodies and antigen-binding fragments thereof. A full-length antibody comprises two heavy chains and two light chains. The variable regions of the light and heavy chains are responsible for antigen binding. The variable region in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ, heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody binds. Two antibodies may bind the same epitope within an antigen if they exhibit competitive binding for the antigen.

As use herein, the term "specifically binds" or "specific for" refers to measurable and reproducible interactions, such as binding between a target and an antibody that is determinative of the presence of the target in the presence of a heterogeneous population of molecules, including biological molecules. For example, an antibody that specifically binds to a target (which can be an epitope) is an antibody that binds this target with greater affinity, avidity, more readily, and/or with greater duration than its bindings to other targets. In some embodiments, an antibody that specifically binds to an antigen reacts with one or more antigenic determinants of the antigen with a binding affinity that is at least about 10 times its binding affinity for other targets.

As used herein, the term "CDR" or "complementarity determining region" is intended to mean the non-contiguous antigen combining sites found within the variable region of both heavy and light chain polypeptides.

The terms "Fc receptor" or "FcR" are used to describe a receptor that binds to the Fc region of an antibody. In some embodiments, an FcR of this invention is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. The tem' includes allotypes, such as FcγRIIIA allotypes: FcγRIIIA-Phe158, FcγRIIIA-Val158, FcγRIIA-R131 and/or FcγRIIA-H131. Other FcRs, including those to be identified in the future, are encompassed by the term "FcR" herein. The term also includes the neonatal receptor, FcRn, which is responsible for the transfer of maternal IgGs to the fetus.

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

The term "analyte" as used herein refers to a molecule, which has a functional attribute of an interaction-blocking characteristic to a molecular binding pair. In some embodiments, the analyte is a neutralizing (or blocking) antibody, e.g., an antibody that interrupts the interaction of two or more molecular components such as a viral protein and a cell-surface protein in a host. In some embodiments, the neutralizing antibody is an anti-coronavirus neutralizing antibody, such as an anti-SARS-CoV-2 neutralizing antibody. In some embodiments, the neutralizing antibody is an anti-RBD neutralizing antibody, wherein the RBD is from a coronavirus, such as SARS-CoV-2 or SAR-CoV. In some embodiments, the neutralizing antibody is an anti-NTD neutralizing antibody, wherein the NTD is from a coronavirus, such as SARS-CoV-2 or SAR-CoV. In some embodiments, the analyte is a small molecule. In some embodiments, the analyte is a polypeptide. In some embodiments, the analyte is a nucleic acid, such as DNA or RNA.

The term "individual" refers to a mammal and includes, but is not limited to, human, bovine, horse, feline, canine, rodent, or primate.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting and the scope of the application is intended to encompass all equivalents, alternatives, and modifications, either generally known, or incorporated here. Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described. It will also be understood by those skilled in the art that changes in the form and details of the subject matter described herein may be made without departing from the scope of this disclosure. In addition, although various advantages, aspects, and objects have been described with reference to various implementations, the scope of this disclosure should not be limited by reference to such advantages, aspects, and objects. The scope of this disclosure should be determined with, e.g., reference to the appended claims.

II. Test Strips

One aspect of the present application provides test devices (such as test strips) for detection of an analyte that blocks binding of a first molecular component and a second molecular component of a molecular binding pair. In some embodiments, the test strip comprises: (a) a chromatographic strip comprising a test zone, such as a first test zone, wherein a first molecular component of a molecular binding pair is immobilized within the first test zone; and (b) a sample binding zone comprising a binding pad, wherein the binding pad comprises a second molecular component of the molecular binding pair, the second molecular component labeled with a detection agent. In some embodiments, the test strip further comprises an absorbent zone comprising a wicking pad. In some embodiments, the test strip further comprises a sample addition zone comprising a sample pad. As described in more detail herein, the components of the test strip are configured, in part, to provide a functional attribute such as directional fluid flow. In some embodiments, two or more components of the test strip are in capillary communication. Components of the test strips and components associated with use of the test strips are discussed in more detail below. The modular description of certain components should not be construed as limiting the scope of the present application. One of ordinary skill in the art will appreciate the various configurations of the components encompassed within the scope of this application based on the teachings herein.

A. Molecular Binding Systems

The test strips described herein are suitable for analyzing a wide variety of molecular binding systems, such as molecular binding pairs, to detect the presence or absence of an analyte that modulates the interaction or association of two or more molecular components of the molecular binding system. In some embodiments, the analyte blocks the binding of molecular components of a molecular binding system. In some embodiments, the analyte enables (and/or enhances) the binding of molecular components of a molecular binding system. Generally, each molecular component of the molecular binding system is designed to evaluate scientifically and/or biologically relevant interactions and associations, and it may not be necessary to replicate the entire biological system. For example, the test strip may comprise a molecular component comprising a first portion comprising at least a part of a molecule of interest having modulated interactions or associations caused by the analyte, such as a first portion comprising at least a part of a naturally occurring ligand or receptor (such as a fragment). In some embodiments, the molecular component comprises an epitope of a molecule of interest. In some embodiments, the portion of the molecular component having modulated interactions or associations caused by the analyte does not comprise an antibody or a fragment thereof. In some embodiments, the molecular component comprises a second portion comprising a molecule (such as an affinity tag) useful for conducting the assays described herein (e.g., a portion of an organism-specific Fc-region, such as a functional Fc fragment, or an enzyme that can later be used to capture the complex in a portion of the test device). Thus, in some embodiments, the molecular component of the molecular binding system comprises a first portion comprising at least a part of a molecule of interest having modulated interactions or associations caused by the analyte and a second portion comprising a molecule (such as an affinity tag) useful for conducting the assays described herein, such as at least a portion of an antibody. In some embodiments, the portions of a molecular component are linked (e.g., cross-linked) or fused. In some embodiments, the molecular component is a fusion polypeptide (e.g., at least a portion of a Fc region, such as a functional Fc fragment, fused to at least a portion of a protein receptor). In some embodiments, the molecular component and the molecule (such as an affinity tag) useful for conducting the assay (e.g., a portion of an organism-specific Fc-region, such as a functional Fc fragment, or an enzyme) are each independently conjugated to a label, such as a detection particle. In some embodiments, the molecular binding system comprises molecular components to test for the presence of a binding agent (such as a neutralizing antibody) specific to one or more epitopes.

In some embodiments, the molecular component does not comprise an antibody. In some embodiments, the molecular component does not comprise an antibody fragment.

In some embodiments, the molecular binding system comprises two or more molecular components. In some embodiments, the molecular binding system comprises two or more molecular components comprising portions thereof from the same molecule of interest. For example, in some embodiments, the molecular binding pair comprises a first molecular component and a second molecular component, wherein the first molecular component and the second molecular component comprise the same polypeptide (or are intended to model the same molecular component, such as a homo-protein-protein interaction). In some embodiments, the molecular binding system comprises two or more molecular components comprising portions thereof from different molecules of interest. For example, in some embodiments, the molecular binding pair comprises a first molecular component and a second molecular component, wherein the first molecular component and the second molecular component comprise different molecules of interest. For example, in some embodiments, the molecular binding pair comprises a first molecular component and a second molecular component, wherein the first molecular component and the second molecular component comprise different polypeptides (e.g., hetero-protein-protein interaction).

In some embodiments, the molecular components of the molecular binding systems encompassed by the description herein are suitable for use in a lateral flow assay. For example, in some embodiments, at least one of the molecular components is mobile in one or more components of a test strip described herein (e.g., chromatographic strip, binding pad, sample pad) when carried by a fluid.

Generally, the test strips described herein may be configured such that any one of the molecular components of a molecular binding system is immobilized in a test zone of a chromatographic strip. For example, for a molecular binding pair comprising a first molecular component and a second molecular component, a first chromatographic strip comprises a test zone comprising the first molecular component immobilized therein. In such a configuration, the second molecular component is a mobile component of the assay. In some embodiments, a second chromatographic strip comprises a test zone comprising the second molecular component immobilized therein. In such a configuration, the first molecular component is a mobile component of the assay.

In some embodiments, the test strips described herein comprise a molecular component labeled with a detection agent. In some embodiments, the molecular component of a molecular binding system (such as a second molecular component of a molecular binding pair) that is not immobilized in a test zone is labeled with a detection agent.

In some embodiments, the molecular binding pair comprises: (i) a viral-surface polypeptide or a fragment thereof; and (ii) a cell-surface polypeptide or a fragment thereof. In some embodiments, the viral-surface polypeptide is a polypeptide, or a fragment thereof, involved with host cell interaction and/or entry. In some embodiments, the viral-surface polypeptide is a viral spike polypeptide, such as a viral spike glycoprotein, or a fragment thereof. In some embodiments, the viral spike protein is a SARS-CoV-2 spike protein or a fragment thereof. In some embodiments, the SAR-CoV-2 spike protein is P0DTC2 or a fragment thereof (according to the Uniprot database, accessed May 19, 2020). In some embodiments, the viral-surface polypeptide comprises a receptor-binding domain (RBD), or a fragment thereof, of a viral spike protein. In some embodiments, the RBD is from a coronavirus. In some embodiments, the RBD is from SARS-CoV-2 (also known as 2019 novel coronavirus, 2019-nCoV) or SAR-CoV. In some embodiments, the viral-surface polypeptide comprises a N-terminal domain (NTD), or a fragment thereof, of a viral spike protein. In some embodiments, the NTD is from a coronavirus. In some embodiments, the NTD is from SARS-CoV-2 (also known as 2019 novel coronavirus, 2019-nCoV) or SAR-CoV. In some embodiments, the cell-surface polypeptide is a cell-membrane protein or a fragment thereof. In some embodiments, the cell-surface polypeptide is a cellular receptor or a fragment thereof. In some embodiments, the cell-surface polypeptide comprises angiotensin-converting enzyme 2 (ACE2) or a fragment thereof. In some embodiments, the cell-surface polypeptide is Q9BYF1 or a fragment thereof (according to the Uniprot database, accessed May 19, 2020).

In some embodiments, the viral-surface polypeptide is derived from a virus selected from the group consisting of severe acute respiratory syndrome (SARS) coronavirus, SARS-CoV-2, Middle East respiratory syndrome (MERS), influenza viruses, such as influenza type A viruses, including subtypes H1N1 and H5N1, human immunodeficiency virus type 1 and type 2 (HIV-1 and HIV-2), human T-cell lymphotropic virus type I and type II (HTLV-I and HTLV-II), hepatitis A virus, hepatitis B virus (HBV), hepatitis C virus (HCV), hepatitis delta virus (HDV), hepatitis E virus (HEV), hepatitis G virus (HGV), parvovirus B19 virus, hepatitis A virus, hepatitis G virus, hepatitis E virus, transfusion transmitted virus (TTV), Epstein-Barr virus, human cytomegalovirus type 1 (HCMV-1), human herpesvirus type 6 (HHV-6), human herpesvirus type 7 (HHV-7), human herpesvirus type 8 (HHV-8), human metapneumovirus, hantavirus, and RNA viruses from Arenaviridae (e.g., Lassa fever virus (LFV)), Pneumoviridae (e.g., human metapneumovirus), Filoviridae (e.g., Ebola virus (EBOV), Marburg virus (MBGV) and Zika virus); Bunyaviridae (e.g., Rift Valley fever virus (RVFV), Crimean-Congo hemorrhagic fever virus (CCHFV), and hantavirus); Flaviviridae (West Nile virus (WNV), Dengue fever virus (DENV), yellow fever virus (YFV), GB virus C (GBV-C; formerly known as hepatitis G virus (HGV)); Rotaviridae (e.g., rotavirus), and combinations thereof.

In some embodiments, the viral-surface polypeptide is derived from a virus of the orthocoronavirinae family. Genetically diverse orthocoronavirinae family is divided into four genera (alpha, beta, gamma, and delta coronaviruses). Human CoVs are limited to the alpha and beta subgroups. Exemplary human CoVs include severe acute respiratory syndrome coronavirus-2 (SARS-CoV-2), severe acute respiratory syndrome coronavirus (SARS-CoV), Middle East respiratory syndrome coronavirus (MERS-CoV), HCoV-229E, HCoV-OC43, HCoV-NL63, and HCoV-HKU1.

Zoonotic CoVs have a natural predilection for emergence into new host species giving rise to new diseases most recently exemplified in humans by severe acute respiratory syndrome coronavirus 2 (SARS-CoV-2), severe acute respiratory syndrome coronavirus (SARS-CoV), and Middle East respiratory syndrome coronavirus (MERS-CoV). Interestingly, all known human CoVs are thought to have emerged as zoonoses from wild or domestic animals.

Nonlimiting examples of subgroup 1a alphacoronaviruses and their GenBank Accession Nos. include FCov.FIPV.79.1146.VR.2202 (NV_007025), transmissible gastroenteritis virus (TGEV) (NC_002306; Q811789.2; DQ811786.2; DQ811788.1; DQ811785.1; X52157.1; AJ011482.1; KC962433.1; AJ271965.2; JQ693060.1; KC609371.1; JQ693060.1; JQ693059.1; JQ693058.1; JQ693057.1; JQ693052.1; JQ693051.1; JQ693050.1); porcine reproductive and respiratory syndrome virus (PRRSV) (NC_001961.1; DQ811787), as well as any subtype, clade or sub-clade thereof, including any other subgroup 1a coronavirus now known (e.g., as can be found in the GenBank® Database) or later identified in the GenBank® Database.

Nonlimiting examples of a subgroup 1b alphacoronaviruses and their GenBank Accession Nos. include HCoV.NL63.Amsterdam.I (NC_005831), BtCoV.HKU2.HK.298.2006 (EF203066), BtCoV.HKU2.HK.33.2006 (EF203067), BtCoV.HKU2.HK.46.2006 (EF203065), BtCoV.HKU2.GD.430.2006 (EF203064), BtCoV.1A.AFCD62 (NC_010437), BtCoV.1B.AFCD307 (NC_010436), BtCov.HKU8.AFCD77 (NC_010438), BtCoV.512.2005 (DQ648858); porcine epidemic diarrhea viruses (NC_003436, DQ355224.1, DQ355223.1, DQ355221.1, JN601062.1, JN601061.1, JN601060.1, JN601059.1, JN601058.1, JN601057.1, JN601056.1, JN601055.1, JN601054.1, JN601053.1, JN601052.1, JN400902.1, JN547395.1, FJ687473.1, FJ687472.1, FJ687471.1, FJ687470.1, FJ687469.1, FJ687468.1, FJ687467.1, FJ687466.1, FJ687465.1, FJ687464.1, FJ687463.1, FJ687462.1, FJ687461.1, FJ687460.1, FJ687459.1, FJ687458.1, FJ687457.1, FJ687456.1, FJ687455.1, FJ687454.1, FJ687453.1, FJ687452.1, FJ687451.1, FJ687450.1, FJ687449.1, AF500215.1, KF476061.1, KF476060.1, KF476059.1, KF476058.1, KF476057.1, KF476056.1, KF476055.1, KF476054.1, KF476053.1, KF476052.1, KF476051.1, KF476050.1, KF476049.1, KF476048.1, KF177258.1, KF177257.1, KF177256.1, KF177255.1), HCoV.229E (NC_002645), as well as any subtype, clade or sub-clade thereof, including any other subgroup 1b coronavirus now known (e.g., as can be found in the GenBank® Database) or later identified in the GenBank® Database.

Nonlimiting examples of subgroup 2a betacoronaviruses and their GenBank Accession Nos. include HCoV.HKU1.C.N5 (DQ339101), MHV.A59 (NC_001846), PHEV.VW572 (NC_007732), HCoV.OC43.ATCC.VR.759 (NC_005147), bovine enteric coronavirus (BCoV.ENT) (NC_003045), as well as any subtype, clade or sub-clade thereof, including any other subgroup 2a coronavirus now known (e.g., as can be found in the GenBank® Database) or later identified in the GenBank Database.

Nonlimiting examples of subgroup 2b betacoronaviruses and their GenBank Accession Nos. include human SARS CoV-2 isolates, such as Wuhan-Hu-1 (NC_045512.2) and any CoV-2 isolates comprising a genomic sequence set forth in GenBank Accession Nos., such as MT079851.1, MT470137.1, MT121215.1, MT438728.1, MT470115.1, MT358641.1, MT449678.1, MT438742.1, LC529905.1, MT438756.1, MT438751.1, MT460090.1, MT449643.1, MT385425.1, MT019529.1, MT449638.1, MT374105.1, MT449644.1, MT385421.1, MT365031.1, MT385424.1, MT334529.1, MT466071.1, MT461669.1, MT449639.1, MT415321.1, MT385430.1, MT135041.1, MT470179.1, MT470167.1, MT470143.1, MT365029.1, MT114413.1, MT192772.1, MT135043.1, MT049951.1; human SARS CoV-1 isolates, such as SARS CoV.A022 (AY686863), SARSCoV.CUHK-W1 (AY278554), SARSCoV.GD01 (AY278489), SARSCoV.HC.SZ.61.03 (AY515512), SARS-CoV.SZ16 (AY304488), SARSCoV.Urbani (AY278741), SARSCoV.civet010 (AY572035), SARSCoV.MA.15 (DQ497008); bat SARS CoV isolates, such as BtSAR-S.HKU3.1 (DQ022305), BtSARS.HKU3.2 (DQ084199), BtSARS.HKU3.3 (DQ084200), BtSARS.Rm1 (DQ412043), BtCoV.279.2005 (DQ648857), BtSARS.Rfl (DQ412042), BtCoV.273.2005 (DQ648856), BtSARS.Rp3 (DQ071615),), as well as any subtype, clade or sub-clade thereof, including any other subgroup 2b coronavirus now known (e.g., as can be found in the GenBank® Database) or later identified in the GenBank® Database.

Nonlimiting examples of subgroup 2c betacoronaviruses and their GenBank Accession Nos. include Middle East respiratory syndrome coronavirus (MERS) isolates, such as Riyadh_2_2012 (KF600652.1), Al-Hasa_18_2013 (KF600651.1), Al-Hasa_17_2013 (KF600647.1), Al-Hasa_15_2013 (KF600645.1), Al-Hasa_16_2013 (KF600644.1), Al-Hasa_21_2013 (KF600634), Al-Hasa_19_2013 (KF600632), Buraidah_1_2013 (KF600630.1), Hafr-Al-Batin_1_2013 (KF600628.1), Al-Hasa_12_2013 (KF600627.1), Bishaltoreq._1_2012 (KF600620.1), Riyadh_3_2013 (KF600613.1), Riyadh_1_2012 (KF600612.1), Al-Hasa32013 (KF186565.1), Al-Hasa_1_2013 (KF186567.1), Al-Hasa_2_2013 (KF186566.1), Al-Hasa_4_2013 (KF186564.1); Betacoronavirus England 1-N1 (NC_019843), SA-N1 (KC667074); human betacoronavirus 2c Jordan-N3/2012 (KC776174.1); human betacoronavirus 2c EMC/2012, (JX869059.2); any bat coronavirus subgroup 2c isolate, such as bat coronavirus Taper/CII_KSA287/Bisha/Saudi Arabia (KF493885.1), bat coronavirus Rhhar/CIIKSA 003/Bisha/Saudi Arabia/2013 (KF493888.1), bat coronavirus Pikuh/CII_KSA_001/Riyadh/Saudi Arabia/2013 (KF493887.1), bat coronavirus Rhhar/CII_KSA_002/Bisha/Saudi Arabia/2013 (KF493886.1), bat coronavirus Rhhar/CII_KSA_004/Bisha/Saudi Arabia/2013 (KF493884.1), bat coronavirus BtCoV.HKU4.2 (EF065506), bat coronavirus BtCoV.HKU4.1 (NC_009019), bat coronavirus BtCoV.HKU4.3 (EF065507), bat coronavirus BtCoV.HKU4.4 (EF065508), bat coronavirus BtCoV133.2005 (NC_008315), bat coronavirus BtCoV.HKU5.5 (EF065512), bat coronavirus BtCoV.HKU5.1 (NC_009020), bat coronavirus BtCoV.HKU5.2 (EF065510), bat coronavirus BtCoV.HKU5.3 (EF065511), and bat coronavirus HKU5 isolate (KC522089.1); any additional subgroup 2c, such as KF192507.1, KF600656.1, KF600655.1, KF600654.1, KF600649.1, KF600648.1, KF600646.1, KF600643.1, KF600642.1, KF600640.1, KF600639.1, KF600638.1, KF600637.1, KF600636.1, KF600635.1, KF600631.1, KF600626.1, KF600625.1, KF600624.1, KF600623.1, KF600622.1, KF600621.1, KF600619.1, KF600618.1, KF600616.1, KF600615.1, KF600614.1, KF600641.1, KF600633.1, KF600629.1, KF600617.1, KC869678.2, KC522088.1, KC522087.1, KC522086.1, KC522085.1, KC522084.1, KC522083.1, KC522082.1, KC522081.1, KC522080.1, KC522079.1, KC522078.1, KC522077.1, KC522076.1, KC522075.1, KC522104.1, KC522104.1, KC522103.1, KC522102.1, KC522101.1, KC522100.1, KC522099.1, KC522098.1, KC522097.1, KC522096.1, KC522095.1, KC522094.1, KC522093.1, KC522092.1, KC522091.1, KC522090.1, KC522119.1, KC522118.1, KC522117.1, KC522116.1, KC522115.1, KC522114.1, KC522113.1, KC522112.1, KC522111.1, KC522110.1, KC522109.1, KC522108.1, KC522107.1, KC522106.1, KC522105.1); *Pipistrellus* bat coronavirus HKU4 isolates (KC522048.1, KC522047.1, KC522046.1, KC522045.1, KC522044.1, KC522043.1, KC522042.1, KC522041.1, KC522040.1, KC522039.1, KC522038.1, KC522037.1, KC522036.1, KC522048.1, KC522047.1, KC522046.1, KC522045.1, KC522044.1, KC522043.1, KC522042.1, KC522041.1, KC522040.1, KC522039.1, KC522038.1, KC522037.1, KC522036.1, KC522061.1, KC522060.1, KC522059.1, KC522058.1, KC522057.1, KC522056.1, KC522055.1, KC522054.1, KC522053.1, KC522052.1, KC522051.1, KC522050.1, KC522049.1, KC522074.1, KC522073.1, KC522072.1, KC522071.1, KC522070.1, KC522069.1, KC522068.1, KC522067.1, KC522066.1, KC522065.1, KC522064.1, KC522063.1, KC522062.1), as well as any subtype, clade or sub-clade thereof, including any other subgroup 2c coronavirus now known (e.g., as can be found in the GenBank® Database) or later identified in the GenBank® Database.

Nonlimiting examples of subgroup 2d betacoronaviruses and their GenBank Accession Nos. include BtCoV.HKU9.2 (EF065514), BtCoV.HKU9.1 (NC_009021), BtCoV.HKU9.3 (EF065515), BtCoV.HKU9.4 (EF065516), as well as any subtype, clade or sub-clade thereof, including any other subgroup 2d coronavirus now known (e.g., as can be found in the GenBank® Database) or later identified in the GenBank® Database.

Nonlimiting examples of subgroup 3 gammacoronaviruses include IBV.Beaudette.IBV.p65 (DQ001339) or any other subgroup 3 coronavirus now known (e.g., as can be found in the GenBank® Database) or later identified in the GenBank® Database.

B. Analytes

The test strips described herein are capable of detecting a functional attribute of an analyte, e.g., an interaction-blocking characteristic. For example, in some embodiments, the test strip detects the presence of an analyte that blocks binding of a first molecular component and a second molecular component of a molecular binding pair. In some embodiments, the presence of an analyte is detected indirectly, e.g., the presence of the analyte is detected based on the modulation of an interaction of a first molecular component and a second molecular component of a molecular binding pair. In some embodiments, the test strip is capable of detecting the presence of any type of analyte, wherein the analyte is suitable for use in a lateral flow assay. For example, in some embodiments, the analyte is mobile in one or more components of a test strip described herein (e.g., chromatographic strip, binding pad, sample pad).

In some embodiments, the analyte is a neutralizing (or blocking) antibody, e.g., an antibody that interrupts the interaction of two or more molecular components such as a viral protein and a cell-surface protein in a host. In some embodiments, the neutralizing antibody is an anti-coronavirus neutralizing antibody. In some embodiments, the neutralizing antibody is an anti-SARS-CoV-2 neutralizing antibody. In some embodiments, the neutralizing antibody is an anti-RBD neutralizing antibody, wherein the RBD is from a coronavirus, such as SARS-CoV-2 or SAR-CoV. In some embodiments, the neutralizing antibody is an anti-NTD neutralizing antibody, wherein the NTD is from a coronavirus, such as SARS-CoV-2 or SAR-CoV.

In some embodiments, the analyte comprises a small molecule. In some embodiments, the analyte comprises a polypeptide. In some embodiments, the analyte comprises a nucleic acid, such as DNA or RNA.

C. Chromatographic Strip

The devices described herein comprise a chromatographic strip comprising one or more test zones, and optionally one or more control zones. As described herein, in some embodiments, the first end region (i.e., the proximal region) is closer to sample adding position than the second end region (i.e., the distal region), e.g., the sample or components thereof flow in a proximal region-to-distal region direction.

In some embodiments, the chromatographic strip is a membrane. In some embodiments, the chromatographic strip is a porous membrane. The pore size of the chromatographic strip may vary widely. In some embodiments, the chromatographic strip comprises pores of about 1 µm to about 20 µm, such any of about 1 µm to about 10 µm, about 5 µm to about 15 µm, or about 10 µm to about 20 µm. In some embodiments, the chromatographic strip comprises a bibulous material. In some embodiments, the chromatographic strip comprises a non-bibulous material. In some embodiments, the chromatographic strip comprises a material selected from the group consisting of a cellulose, cellulose blend, nitrocellulose (such as a nitrocellulose membrane), cellulose ester, mixed nitrocellulose ester, polyester, acrylonitrile copolymer, rayon, glass fiber, polyethylene terephthalate fibers, polypropylene, and combinations thereof. In some embodiments, the membrane is a nitrocellulose membrane.

In some embodiments, the chromatographic strip, or a portion thereof, is treated with a blocker, e.g., to increase specificity of any binding interactions. In some embodiments, the blocker comprises casein, bovine serum albumin (BSA), methylated BSA, whole animal serum, non-fat dry milk, or a combination thereof. When the chromatographic strip is blocked, the charge of a chromatographic strip, such as nitrocellulose, is neutralized and thus, no additional proteins or components thereof can bind to the blocked chromatographic strip. Additionally, the chromatographic structure of the chromatographic strip is altered and the flow may be more like a gliding or sliding flow instead of the flow of traditional chromatography.

In some embodiments, the molecular component and/or a binding agent, such as an antibody or fragment thereof, are treated prior to being applied to the chromatographic strip, such as in a test zone or a control zone. In some embodiments, the molecular component and/or a binding agent, such as an antibody or fragment thereof, are treated with trehalose (e.g., about 2%) and sucrose (e.g., about 10%) prior to being applied to the chromatographic strip.

i. Test zones

The one or more test zones of the chromatographic strips described herein are configured to enable a location-specific indication of the presence or absence of an analyte in a sample. Generally, the one or more test zones of the chromatographic strips described herein comprise an immobilized molecular component capable of associating with, such as binding, another molecular component of a molecular binding system. In some embodiments, for a molecular binding pair comprising a first molecular component and a second molecular component, the chromatographic strip comprises a test zone having the first molecular component immobilized therein. In some embodiments, the first molecular component is directly immobilized in the test zone, e.g., via a direct associate or cross-linking. In some embodiments, the first molecular component is indirectly immobilized in the test zone, e.g., via binding of a molecule having affinity for the first molecular component such as an antibody.

In some embodiments, the test zone comprises an anti-human Ig binding agent, such as an anti-human-IgG binding agent or an anti-human-IgG binding agent. In some embodiments, the chromatographic strip comprises a plurality of test zones, wherein a test zone comprises an anti-human-IgG binding agent, such as an anti-human-IgG binding agent, and wherein another test zone comprises an anti-human-IgM binding agent, such as an anti-human IgM binding agent.

The test zones described herein may be in any shape or size. In some embodiments, the test zone is designed such that a substantial portion of a fluid comprising a sample, or components thereof, will pass through when the chromatographic strip is used. In some embodiments, the test zone is designed for readability of a result associated with the test zone. In some embodiments, the test zone is a line positioned across the chromatographic strip substantially perpendicular to the direction of fluid flow. In some embodiments, the test line is at least about 0.1 mm in width.

In some embodiments, the chromatographic strip comprises more than one test zone. In such instances, the sequence of test zones (in relation to the directional flow of sample in the chromatographic strip) is arranged in an order based on the potential chronological depletion of one or more components from the sample during the analysis.

ii. Control Zones

When present, the one or more control zones of the chromatographic strips described herein are configured to enable a location-specific indication of the presence or absence of a component of a sample and/or a component included in the test strip (e.g., to ensure proper operation of the test strip).

In some embodiments, the control zone comprises an immobilized capture agent, such as an antibody or an antigen-binding fragment, specific for a component of sample and/or a component included in the test strip. In some embodiments, the control capture agent binds to an aspect of a molecular component that does not interaction with or associate directly with another molecular component of a molecular system, e.g., the affinity tag or detection agent. In some embodiments, the immobilized control capture agent is specific for an organism-specific Ig molecule, such as an anti-mouse-Ig antibody or antigen-binding fragment. In some embodiments, the immobilized control capture agent is specific for an organism-specific Ig class molecule, such as an anti-human-IgG antibody or antigen-binding fragment. In some embodiments, the immobilized control capture agent is specific for a feature included in a molecular component of the test strip, such as when a molecular component comprises a mouse-Fc region, or a fragment thereof, the control capture agent is specific for the mouse-Fc region, e.g., an anti-mouse Ig or Fc receptor. In some embodiments, the immobilized control capture agent is specific for a component included in the test strip, such as when an organism-specific anti-human antibody or antigen-binding fragment is included in the test strip the control capture agent is specific for the organism-specific antibody or antigen-binding fragment. The test strips described herein are designed such that control zones provide relevant information of the assay, and immobilized features in the control zones are selected accordingly. In some embodiments, the control capture agent is directly immobilized in the control zone, e.g., via a direct associate or cross-linking. In some embodiments, the control capture agent is indirectly immobilized in the control zone, e.g., via binding of a molecule having affinity for the control capture agent such as an antibody.

The control zones described herein may be any shape or size. In some embodiments, the control zone is designed such that a substantial portion of a fluid comprising a sample, or components thereof, will pass through when the chromatographic strip is used. In some embodiments, the control zone is designed for readability of a result associated with the control zone. In some embodiments, the control zone is a line positioned across the chromatographic strip substantially perpendicular to the direction of fluid flow. In some embodiments, the control line is at least about 0.1 mm in width.

In some embodiments, when the chromatographic strip comprises one or more test zones and one or more control zones, the sequence of the one or more test zones and one or more control zones (in relation to the directional flow of sample in the chromatographic strip) is arranged in an order based on the potential chronological depletion of one or more components from the sample during the analysis.

D. Sample Binding Zone

The test strips described herein comprise a sample binding zone comprising a binding pad, as also referred to as a conjugation pad. In some embodiments, the binding pad comprises a molecular component, such as a molecular component labeled with a detection agent. In some embodiments, the sample binding zone further comprises another component (e.g., an antibody or antigen binding fragment), such as an organism-specific anti-Ig binding agent, e.g., a mouse anti-human Ig antibody or antigen-binding fragment or a mouse anti-human class specific Ig antibody or antigen-binding fragment. In some embodiments, the other component (e.g., an antibody or antigen binding fragment) is mobile in the test strip such that in the presence of a fluid the other will travel downstream in the test strip. In some embodiments, the other component (e.g., an antibody or antigen binding fragment) is labeled with a detection agent.

In some embodiments, the components of the binding pad are pre-loaded therein, such as impregnated). In some embodiments, the components of the binding pad are mobile in the binding pad such that in the presence of a fluid the components will travel downstream in the test strip.

In some embodiments, the binding zone, including the binding pad, is configured such that a sample and/or reagent may be added directly thereto. In some embodiments, the binding zone is configured to filter certain components of a sample, e.g., cells or cellular debris.

In some embodiments, the binding pad is in capillary communication with a chromatographic strip. In some embodiments, the binding pad is in capillary communication with a sample pad.

i. Detection Agent

Certain components of the test strips described herein comprise a detection agent to facilitate identification (qualitatively and/or quantitatively) of said components at certain zones of the test strips (e.g., a test zone, control zone). In some embodiments, the molecular component of a molecular binding system is a labeled with a detection agent. In some embodiments, the other component such as in the sample binding zone (e.g., an antibody or antigen binding fragment) is labeled with a detection agent. In some embodiments, wherein two or more component of a test strip are labeled with a detection agent, each component is labeled with a unique detection agent that can be differentiated from other detection agents of the test strip (e.g., based on color).

In some embodiments, the detection agent comprises an enzyme. In some embodiments, the detection agent comprises a polymeric enzyme comprising a plurality of enzymes. In some embodiments, the enzyme is selected from the group consisting of beta-D-galactosidase, glucose oxidase, horseradish peroxidase, alkaline phosphatase, beta-lactamase, glucose-6-phosphate dehydrogenase, urease, uricase, superoxide dismutase, luciferase, pyruvate kinase, lactate dehydrogenase, galactose oxidase, acetylcholinesterase, enterokinase, tyrosinase, and xanthine oxidase.

In some embodiments, the detection agent comprises a detection particle. In some embodiments, the detection particle comprises an enzymatic particle (such as a nanoparticle), polystyrene particle (such as a microsphere), latex particle, particle comprising gold (such as a nano-gold particle or gold nanoparticle), colloidal gold particle, metal particle (such as an iron oxide nanoparticle), magnetic particle, fluorescently detectable particle, or semi-conductor particle (such as a nanocrystal). In some embodiments, the size of the detection particle (such as measured by an average or mean size of a population of detection particles is based, at least in part, on the pore size of the chromatography strip and/or visibility of the detection particle. For example, in some embodiments, the detection particle is about 5 μm to about 100 μm, such as any of about 20 μm to about 100 μm, about 40 μm to about 80 μm, or about 50 μm to about 70 μm. In some embodiments, the detection particle is less than about 100 μm, such as less than about any of 90 μm, 80 μm, 70 μm, 60 μm, 50 μm, 40 μm, 30 μm, 20 μm, or 10 μm. In some embodiments, the detection particle is about any of 100 μm, 90 μm, 80 μm, 70 μm, 60 μm, 50 μm, 40 μm, 30 μm, 20 μm, or 10 μm. In some embodiments, the detection agent comprises an enzyme. In some embodiments, the detection particle can also serve as an affinity tag that can later be used for capture in a portion of the test device.

E. Absorbent Zone

In some embodiments, the test strip further comprises an absorbent zone. Generally, the absorbent zone is configured, e.g., to remove excess fluid from the chromatographic strip in a reversible or non-reversible manner. In some embodiments, the absorbent zone is configured to be a reversible desiccant (allowing back flow of fluid from the absorbent zone). In some embodiments, the absorbent zone is configured to be a non-reversible desiccant. In some embodiments, the absorbent zone comprises a wicking pad. In some embodiments, the wicking pad comprises a bibulous material. In some embodiments, the wicking pad comprises a filter paper, glass fiber filter, or the like.

In some embodiments, the absorbent zone is located downstream of the chromatographic strip. In some embodiments, the absorbent zone is in capillary communication with the chromatographic strip.

F. Sample Addition Zone/Sample Pad

In some embodiments, the test strip further comprising a sample addition zone comprising a sample pad. In some embodiments, the sample pad is in capillary communication with one or more downstream components of a test strip, e.g., the binding pad or chromatographic strip.

In some embodiments, the sample addition zone, including the sample pad, is configured to receive a sample. In some embodiments, the sample comprises a bodily fluid. In some embodiments, the sample is a whole blood sample. In some embodiments, the sample is a blood sample. In some embodiments, the blood sample is obtained from a finger prick, such as a lancet finger prick. In some embodiments, the sample addition zone is configured to receive a blood sample obtained from a finger prick. In some embodiments, the sample is a body secretion sample. In some embodiments, the sample is a bronchial alveolar lavage fluid sample.

In some embodiments, the sample pad is configured to receive about 5 µL to about 500 µL of fluid, such as a sample or a buffer.

G. Exemplary Test Strips and Configurations Thereof

In some embodiments, provided herein is a test strip for detection of an analyte that blocks binding of a first molecular component and a second molecular component of a molecular binding pair, the test strip comprising: (a) a chromatographic strip having a first end region and a second end region, wherein the chromatographic strip comprises a first test zone, wherein the first molecular component is immobilized within the first test zone; and (b) a sample binding zone comprising a binding pad having a first end region and a second end region, wherein the binding pad comprises the second molecular component labeled with a detection agent, wherein the first end region of the chromatographic strip is in capillary communication with the second end region of the binding pad. In some embodiments, the molecular binding pair comprises: (i) a viral-surface polypeptide or a fragment thereof; and (ii) a cell-surface polypeptide or a fragment thereof. In some embodiments, the viral-surface polypeptide comprises a receptor-binding domain (RBD) of a spike protein from a virus. In some embodiments, the viral-surface polypeptide comprises a N-terminus domain (NTD) of a spike protein from a virus. In some embodiments, the virus is a coronavirus. In some embodiments, the coronavirus is SARS-CoV-2 or SAR-CoV. In some embodiments, the cell-surface polypeptide is ACE2. In some embodiments, the analyte is a neutralizing antibody.

In some embodiments, provided herein is a test strip for detection of a neutralizing antibody that blocks binding of a first molecular component and a second molecular component of a molecular binding pair, wherein the first molecular component comprises a RBD and/or NTD of a viral spike protein or a fragment thereof and the second molecular component comprises ACE2 or a fragment thereof, the test strip comprising: (a) a chromatographic strip having a first end region and a second end region, wherein the chromatographic strip comprises a first test line and a control line positioned substantially perpendicular to the direction of fluid flow, wherein the first molecular component is immobilized within the first test line, wherein an anti-non-human IgG binding agent is immobilized within the control line, and wherein the first test line is positioned closer to the first end region relative to the positioning of the control line; (b) a sample binding zone comprising a binding pad having a first end region and a second end region, wherein the binding pad comprises the second molecular component fused to at least a portion of a non-human Fc region and labeled with a detection agent, wherein the portion of the non-human Fc region is capable binding the anti-non-human IgG binding agent; (c) a sample addition zone comprising a sample pad; and (d) an absorbent zone comprising a wicking pad, wherein the first end region of the chromatographic strip is in capillary communication with the second end region of the binding pad, wherein the second end region of the chromatographic strip is in capillary communication with the wicking pad, and wherein the sample pad is in capillary communication with the first end region of the binding pad. In some embodiments, the RBD polypeptide is from a coronavirus. In some embodiments, the NTD polypeptide is from a coronavirus. In some embodiments, the coronavirus is SARS-CoV-2 or SAR-CoV. In some embodiments, the ACE2 polypeptide is from human.

In some embodiments, provided herein is a test strip for detection of a neutralizing antibody that blocks binding of a first molecular component and a second molecular component of a molecular binding pair, wherein the first molecular component comprises ACE2 or a fragment thereof and the second molecular component comprises a RBD and/or NTD of a viral spike protein or a fragment thereof, the test strip comprising: (a) a chromatographic strip having a first end region and a second end region, wherein the chromatographic strip comprises a first test line and a control line positioned substantially perpendicular to the direction of fluid flow, wherein the first molecular component is immobilized within the first test line, wherein an anti-non-human IgG binding agent is immobilized within the control line, and wherein the first test line is positioned closer to the first end region relative to the positioning of the control line; (b) a sample binding zone comprising a binding pad having a first end region and a second end region, wherein the binding pad comprises the second molecular component fused to at least a portion of a non-human Fc region and labeled with a detection agent, wherein the portion of the non-human Fc region is capable of binding the anti-non-human IgG binding agent; (c) a sample addition zone comprising a sample pad; and (d) an absorbent zone comprising a wicking pad, wherein the first end region of the chromatographic strip is in capillary communication with the second end region of the binding pad, wherein the second end region of the chromatographic strip is in capillary communication with the wicking pad, and wherein the sample pad is in capillary communication with the first end region of the binding pad. In some embodiments, the RBD polypeptide is from a coronavirus. In some embodiments, the NTD polypeptide is from a coronavirus. In some embodiments, the coronavirus is SARS-CoV-2 or SAR-CoV. In some embodiments, the ACE2 polypeptide is from human.

In some embodiments, provided herein is a test strip for detection of a neutralizing antibody that blocks binding of a first molecular component and a second molecular component of a molecular binding pair, wherein the first molecular component comprises ACE2 or a fragment thereof and the second molecular component comprises a RBD and/or NTD of a viral spike protein or a fragment thereof, the test strip comprising: (a) a chromatographic strip having a first end region and a second end region, wherein the chromatographic strip comprises a first test line, a second test line, and a control line positioned substantially perpendicular to the direction of fluid flow, wherein the first molecular component is immobilized within the first test line, wherein an anti-non-human Ig binding agent is immobilized within the second test line, wherein an anti-non-human (such as rabbit) IgG binding agent is immobilized within the control line, and wherein the first test line, the second test line, and the control line are positioned in order from the first end region to the second end region; (b) a sample binding zone comprising a binding pad having a first end region and a second end region, wherein the binding pad comprises: (i) the second molecular component fused to at least a portion of a non-human (such as rabbit) Fc region and labeled with a detection agent; and (ii) a non-human anti-human Ig binding agent, wherein the portion of the non-human (such as rabbit) Fc region is capable of being bound by the anti-non-human (such as rabbit) IgG binding agent, and the non-human anti-human Ig binding agent is capable of being bound by the anti-non-human Ig binding agent; (c) a sample addition zone comprising a sample pad; and (d) an absorbent zone comprising a wicking pad, wherein the first end region of the chromatographic strip is in capillary communication with the second end region of the binding pad, wherein the second end region of the chromatographic strip is in capillary communication with the wicking pad, and wherein the sample pad is in capillary communication with the first end region of the binding pad. In some embodiments, the RBD polypeptide is from a coronavirus. In some embodiments, the NTD polypeptide is from a coronavirus. In some embodiments, the coronavirus is SARS-CoV-2 or SAR-CoV. In some embodiments, the ACE2 polypeptide is from human.

In some embodiments, provided herein is a test strip for detection of a neutralizing antibody that blocks binding of a first molecular component and a second molecular component of a molecular binding pair, wherein the first molecular component comprises a RBD or a NTD of a viral spike protein or a fragment thereof and the second molecular component comprises ACE2 or a fragment thereof, the test strip comprising: (a) a chromatographic strip having a first end region and a second end region, wherein the chromatographic strip comprises a first test line, a first control line, and a second control line positioned substantially perpendicular to the direction of fluid flow, wherein the first molecular component is immobilized within the first test line, wherein an anti-non-human Ig binding agent is immobilized within the first control line, wherein an anti-non-human (such as rabbit) IgG binding agent is immobilized within the second control line, and wherein the first test line, the second test line, and the control line are positioned in order from the first end region to the second end region; (b) a sample binding zone comprising a binding pad having a first end region and a second end region, wherein the binding pad comprises: (i) the second molecular component fused to at least a portion of a non-human (such as rabbit) Fc region and labeled with a first detection agent; and (ii) a non-human anti-human Ig binding agent labeled with a second detection agent, wherein the portion of the non-human (such as rabbit) Fc region is capable of being bound by the anti-non-human (such as rabbit) IgG binding agent, and the non-human anti-human Ig binding agent is capable of being bound by the anti-non-human Ig binding agent; (c) a sample addition zone comprising a sample pad; and (d) an absorbent zone comprising a wicking pad, wherein the first end region of the chromatographic strip is in capillary communication with the second end region of the binding pad, wherein the second end region of the chromatographic strip is in capillary communication with the wicking pad, and wherein the sample pad is in capillary communication with the first end region of the binding pad. In some embodiments, the RBD polypeptide is from a coronavirus. In some embodiments, the NTD polypeptide is from a coronavirus. In some embodiments, the coronavirus is SARS-CoV-2 or SAR-CoV. In some embodiments, the ACE2 polypeptide is from human.

In some embodiments, provided herein is a test strip for detection of a neutralizing antibody that blocks binding of a first molecular component and a second molecular component of a molecular binding pair, wherein the first molecular component comprises ACE2 or a fragment thereof and the second molecule component comprises a RBD and/or NTD polypeptide of a viral spike protein or a fragment thereof, the test strip comprising: (a) a chromatographic strip having a first end region and a second end region, wherein the chromatographic strip comprises a first test line, a second test line, a third test line, and a control line positioned substantially perpendicular to the direction of fluid flow from the first end region to the second end region, wherein the first molecular component is immobilized within the first test line, wherein an anti-human IgG binding agent is immobilized within the second test line, wherein an anti-human IgM binding agent is immobilized within the third test line, wherein an anti-rabbit IgG binding agent is immobilized within the control line, and wherein the first test line, the second test line, the third test line, and the control line are positioned in order from the first end region to the second end region; (b) a sample binding zone comprising a binding pad having a first end region and a second end region, wherein the binding pad comprises a complex comprising the second molecule component (the RBD and/or NTD polypeptide or the fragment thereof), a rabbit Fc region or a fragment thereof, and a 60 nm gold bead, wherein the portion of the rabbit Fc region or fragment thereof is capable of being bound by the anti-rabbit IgG binding agent; (c) a sample addition zone comprising a sample pad; and (d) an absorbent zone comprising a wicking pad, wherein the first end region of the chromatographic strip is in capillary communication with the second end region of the binding pad, wherein the second end region of the chromatographic strip is in capillary communication with the wicking pad, and wherein the sample pad is in capillary communication with the first end region of the binding pad. In some embodiments, the RBD polypeptide or fragment thereof is from a coronavirus. In some embodiments, the NTD polypeptide or fragment thereof is from a coronavirus. In some embodiments, the coronavirus is SARS-CoV-2 or SAR-CoV. In some embodiments, the ACE2 polypeptide is from human.

H. Illustration of Exemplary Test Strips and Configurations Thereof

Figures of exemplary test strips, and configurations of components therein, are provided to facilitate the understanding and operational aspects of the test strips of the present application, including the integration of components described herein. Such exemplary descriptions are not to be interpreted as limiting the subject matter described herein.

FIG. 1 shows an illustration of an exemplary test strip for detection of an analyte that blocks binding of a first molecular component and a second molecular Component of a molecular binding pair, the test strip comprising: (a) a chromatographic strip 105 having a first end region 110 and a second end region 115, wherein the chromatographic strip 105 comprises a test zone 120; and (b) a sample binding zone comprising a binding pad 125 having a first end region 130 and a second end region 135, wherein the first end region 110 of the chromatographic strip 105 is in capillary communication with the second end region 135 of the binding pad 125. In some embodiments, the first molecular component of the molecular binding pair is immobilized within the test zone 120, and the binding pad 125 comprises the second molecular component of the molecular binding pair, the second molecular component labeled with a detection agent.

When the test strip 100 of FIG. 1 is in operation, a sample, or components thereof, travel via the binding pad 125 to the chromatographic strip 105, and a fluid comprising the sample, or components thereof, and the second molecular component labeled with the detection agent enters the chromatographic strip 105. The fluid then travels in the chromatographic strip 105 in the direction of the second end region 115, including through the test zone 120. In the presence of the analyte that blocks binding of the first molecular component and the second molecular component of the molecular binding pair, the second molecular component labeled with the detection agent is not bound by the immobilized first molecular component in the test zone 120, and thus no detectable signal or only a weakly detectable signal occurs at the test zone 120. In the absence of the analyte that blocks binding of the first molecular component and the second molecular component of the molecular binding pair, the second molecular component labeled with the detection agent is bound by the immobilized first molecular component in the test zone 120, and thus a detectable signal occurs at the test zone 120. In some embodiments, the test strip 100 is configured for quantification of the amount of the analyte that blocks binding of the first molecular component and the second molecular component, e.g., based on the binding of the labeled second molecular component by the immobilized first molecular component in the test zone 120.

Figure 2:
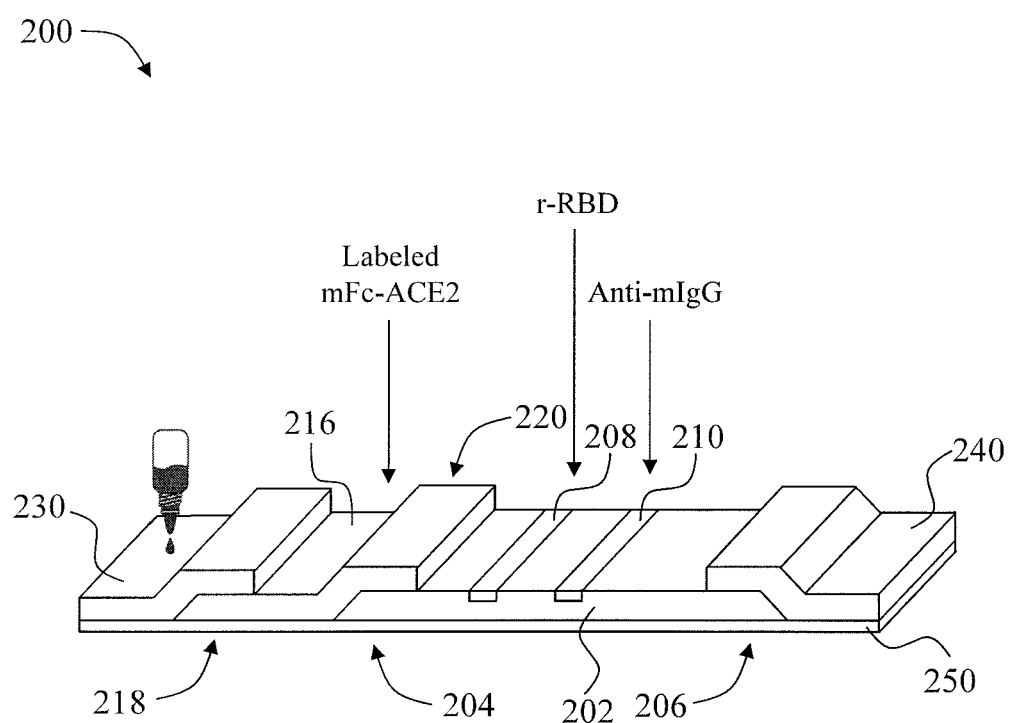
FIG. 2 shows a schematic of an exemplary test strip 200 comprising: (a) a chromatographic strip 202 comprising: (i) a test zone 208 comprising an immobilized recombinant RBD polypeptide (r-RBD), and (ii) a control zone 210 comprising an immobilized anti-mouse IgG binding agent; and (b) a binding pad 216 comprising a mouse Fc-ACE2 fusion polypeptide (mFc-ACE2) labeled with a detection agent.

FIG. 2 shows an illustration of an exemplary test strip 200 for detection of an analyte, such as a neutralizing antibody, that blocks binding of a first molecular component and a second molecular component of a molecular binding pair, wherein the first molecular component comprises a recombinant receptor-binding domain polypeptide (r-RBD) of a viral spike protein, and the second molecular component comprises a mouse-Fc and ACE2 fusion polypeptide (mFc-ACE2). As shown in FIG. 2, the test strip 200 comprises a chromatographic strip 202 having a first end region 204 and a second end region 204, wherein the chromatographic strip 202 comprises a first test line 208 and a control line 210 positioned substantially perpendicular to the direction of fluid flow, wherein the first molecular component (r-RBD) is immobilized within the first test line 208, wherein an anti-mouse IgG binding agent is immobilized within the control line 210, and wherein the first test line 208 is positioned closer to the first end region 204 relative to the positioning of the control line 210 and the first end region 204. As shown in FIG. 2, the test strip comprises a sample binding zone comprising a binding pad 216 having a first end region 218 and a second end region 220, wherein the binding pad 216 comprises the labeled second molecular component (a labeled mouse-Fc-ACE2), and wherein the portion of the mouse-Fc region is capable binding the anti-mouse IgG binding agent. Additionally, the test strip illustrated in FIG. 2 comprises a sample addition zone comprising a sample pad 230, and an absorbent zone comprising a wicking pad 240. The illustrated test strip 200 also comprises a backing card 250 configured to support the other components of the test strip 200. The test strip 200 is configured such that the first end region 204 of the chromatographic strip 202 is in capillary communication with the second end region 220 of the binding pad 216, wherein the second end region 206 of the chromatographic strip 202 is in capillary communication with the wicking pad 240, and wherein the sample pad 230 is in capillary communication with the first end region 218 of the binding pad 216. In some embodiments, the recombinant RBD polypeptide is from a coronavirus. In some embodiments, the coronavirus is SARS-CoV-2 or SAR-CoV. In some embodiments, the ACE2 polypeptide is from human.

When the test strip 200 of FIG. 2 is in operation, a sample, or components thereof, travel via the sample pad 230 to the binding pad 216, and a fluid comprising the sample, or components thereof, and the labeled mFc-ACE2 fusion polypeptide enters the chromatographic strip 202. The fluid then travels via the chromatographic strip 202 from the first end region 204 to the second end region 206, including through the first test line 208. In the presence of the analyte that blocks binding of the first molecular component and the second molecular component of the molecular binding pair, the second molecular component labeled with the detection agent (the labeled mFc-ACE2) is not bound by the immobilized first molecular component (r-RBD) in the first test line 208, and thus no detectable signal or only a weakly detectable signal occurs at the first test line 208. In the absence of the analyte that blocks binding of the first molecular component and the second molecular component of the molecular binding pair, the second molecular component labeled with the detection agent (labeled mFc-ACE2) is bound by the immobilized first molecular component (r-RBD) in the first test line 208, and thus a detectable signal occurs at the first test line 208. The control line 210 comprises immobilized anti-mouse IgG to capture any of the labeled mFc-ACE2 that passes through the first test line 208 to confirm proper operation of the test strip. In some embodiments, the test strip 200 is configured for quantification of the amount of the analyte that blocks binding of the first molecular component and the second molecular component, e.g., based on the binding of the labeled second molecular component in the first test line 208.

Figure 3:
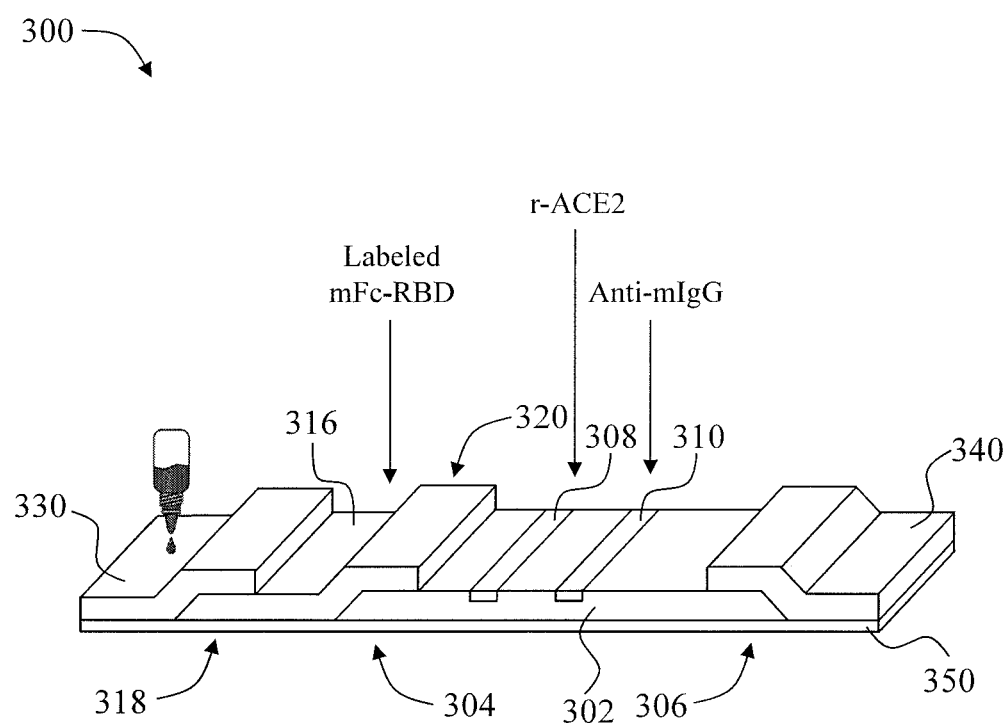
FIG. 3 shows a schematic of an exemplary test strip 300 comprising: (a) a chromatographic strip 302 comprising: (i) a first test line 308 comprising an immobilized recombinant ACE2 polypeptide (r-ACE2), and (ii) a control line 310 comprising an immobilized anti-mouse IgG binding agent; and (b) a binding pad 316 comprising a mouse Fc-RBD fusion polypeptide (mFc-RCD) labeled with a detection agent.

FIG. 3 shows an illustration of an exemplary test strip 300 for detection of an analyte, such as a neutralizing antibody, that blocks binding of a first molecular component and a second molecular component of a molecular binding pair, wherein the first molecular component comprises a recombinant receptor-binding domain polypeptide (r-ACE2), and the second molecular component comprises a mouse-Fc and RBD fusion polypeptide (mFc-RBD). As shown in FIG. 3, the test strip 300 comprises a chromatographic strip 302 having a first end region 304 and a second end region 304, wherein the chromatographic strip 302 comprises a first test line 308 and a control line 310 positioned substantially perpendicular to the direction of fluid flow, wherein the first molecular component (r-ACE2) is immobilized within the first test line 308, wherein an anti-mouse IgG binding agent is immobilized within the control line 310, and wherein the first test line 308 is positioned closer to the first end region 304 relative to the positioning of the control line 310 and the first end region 304. As shown in FIG. 3, the test strip comprises a sample binding zone comprising a binding pad 316 having a first end region 318 and a second end region 320, wherein the binding pad 316 comprises the labeled second molecular component (a labeled mouse-Fc-RBD), and wherein the portion of the mouse-Fc region is capable binding the anti-mouse IgG binding agent. Additionally, the test strip illustrated in FIG. 3 comprises a sample addition zone comprising a sample pad 330, and an absorbent zone comprising a wicking pad 340. The illustrated test strip 300 also comprises a backing card 350 configured to support the other components of the test strip 300. The test strip 300 is configured such that the first end region 304 of the chromatographic strip 302 is in capillary communication with the second end region 320 of the binding pad 316, wherein the second end region 306 of the chromatographic strip 302 is in capillary communication with the wicking pad 340, and wherein the sample pad 330 is in capillary communication with the first end region 318 of the binding pad 316. In some embodiments, the recombinant RBD polypeptide is from a coronavirus. In some embodiments, the coronavirus is SARS-CoV-2 or SAR-CoV. In some embodiments, the ACE2 polypeptide is from human.

When the test strip 300 of FIG. 3 is in operation, a sample, or components thereof, travel via the sample pad 330 to the binding pad 316, and a fluid comprising the sample, or components thereof, and the labeled mFc-RBD fusion polypeptide enters the chromatographic strip 302. The fluid then travels via the chromatographic strip 302 from the first end region 304 to the second end region 306, including through the first test line 308. In the presence of the analyte that blocks binding of the first molecular component and the second molecular component of the molecular binding pair, the second molecular component labeled with the detection agent (the labeled mFc-RBD) is not bound by the immobilized first molecular component (r-ACE2) in the first test line 308, and thus no detectable signal or only a weakly detectable signal occurs at the first test line 308. In the absence of the analyte that blocks binding of the first molecular component and the second molecular component of the molecular binding pair, the second molecular component labeled with the detection agent (labeled mFc-RBD) is bound by the immobilized first molecular component (r-ACE2) in the first test line 308, and thus a detectable signal occurs at the first test line 308. The control line 310 comprises immobilized anti-mouse IgG to capture any of the labeled mFc-RBD that passes through the first test line 308 to confirm proper operation of the test strip. In some embodiments, the test strip 300 is configured for quantification of the amount of the analyte that blocks binding of the first molecular component and the second molecular component, e.g., based on the binding of the labeled second molecular component in the first test line 308.

Figure 4:
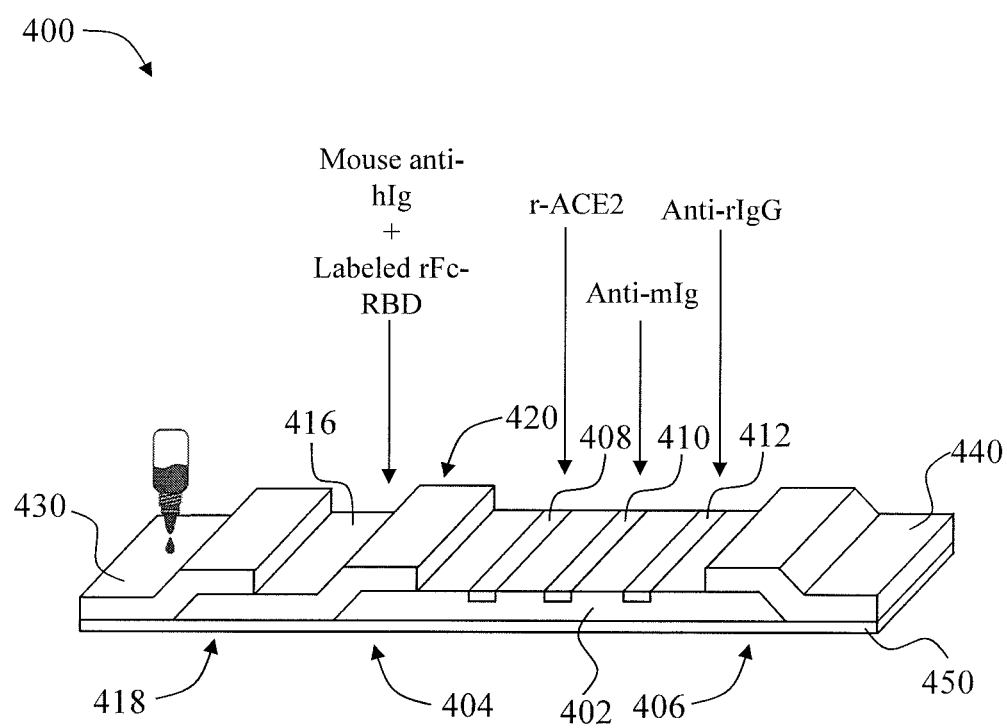
FIG. 4 shows a schematic of an exemplary test strip 400 comprising: (a) a chromatographic strip 402 comprising: (i) a first test line 408 comprising an immobilized recombinant ACE2 polypeptide (r-ACE2), (ii) a second test line 410 comprising an immobilized anti-mouse Ig binding agent (anti-mIg), and (iii) a control line 412 comprising an immobilized anti-rabbit IgG binding agent (anti-rIgG); and (b) a binding pad 416 comprising: (i) a rabbit Fc-RBD fusion polypeptide (rFC-RBD) labeled with a detection agent, and (ii) a mouse anti-human Ig binding agent (mouse anti-hIg).

FIG. 4 shows an illustration of an exemplary test strip 400 for detection of a neutralizing antibody that blocks binding of a first molecular component and a second molecular component of a molecular binding pair, wherein the first molecular component comprises a recombinant ACE2 polypeptide (r-ACE2), and the second molecular component comprises a rabbit-Fc and RBD fusion polypeptide (rFc-RBD). As shown in FIG. 4, the test strip 400 comprises a chromatographic strip 402 having a first end region 404 and a second end region 404, wherein the chromatographic strip 402 comprises a first test line 408, a second test line 410, and a control line 412 positioned substantially perpendicular to the direction of fluid flow, wherein the first molecular component (r-ACE2) is immobilized within the first test line 408, wherein an anti-mouse Ig binding agent is immobilized within the second test line 410, wherein an anti-rabbit IgG binding agent is immobilized within the control line 412, and wherein the first test line 408, the second test line 410, and the control line 412 are positioned in sequential order starting from the first end region 404 of the chromatographic strip 402. As shown in FIG. 4, the test strip comprises a sample binding zone comprising a binding pad 416 having a first end region 418 and a second end region 420, wherein the binding pad 416 comprises the labeled second molecular component (a labeled rFc-RBD) and the mouse anti-hIg binding agent. Additionally, the test strip illustrated in FIG. 4 comprises a sample addition zone comprising a sample pad 430, and an absorbent zone comprising a wicking pad 440. The illustrated test strip 400 also comprises a backing card 450 configured to support the other components of the test strip 400. The test strip 400 is configured such that the first end region 404 of the chromatographic strip 402 is in capillary communication with the second end region 420 of the binding pad 416, wherein the second end region 406 of the chromatographic strip 402 is in capillary communication with the wicking pad 440, and wherein the sample pad 430 is in capillary communication with the first end region 418 of the binding pad 416. In some embodiments, the recombinant RBD polypeptide is from a coronavirus. In some embodiments, the coronavirus is SARS-CoV-2 or SAR-CoV. In some embodiments, the ACE2 polypeptide is from human.

When the test strip 400 of FIG. 4 is in operation, a sample, or components thereof, travel via the sample pad 430 to the binding pad 416, and a fluid comprising the sample, or components thereof, the labeled rFc-RBD fusion polypeptide, and the mouse anti-hIg enters the chromatographic strip 402. The fluid then travels via the chromatographic strip 402 from the first end region 404 to the second end region 406, including through the first test line 408, the second test line 410, and the control line 412. In the presence of the neutralizing antibody that blocks binding of the first molecular component and the second molecular component of the molecular binding pair, the second molecular component labeled with the detection agent (the labeled rFc-RBD) is not bound by the immobilized first molecular component (r-ACE2) in the first test line 408, and thus no detectable signal or only a weakly detectable signal occurs at the first test line 408. In the absence of the neutralizing that blocks binding of the first molecular component and the second molecular component of the molecular binding pair, the second molecular component labeled with the detection agent (labeled rFc-RBD) is bound by the immobilized first molecular component (r-ACE2) in the first test line 408, and thus a detectable signal occurs at the first test line 408. In the presence of the neutralizing antibody that blocks binding of the first molecular component and the second molecular component of the molecular binding pair, a complex comprising the second molecular component labeled with the detection agent (the labeled rFc-RBD), the neutralizing antibody, and the mouse anti-hIG binding agent is formed and can be bound by the immobilized by the immobilized anti-mIG in the second test line, thereby producing a detectable signal at the second test line due to the labeled rFC-RBD. In the absence of the neutralizing antibody that blocks binding of the first molecular component and the second molecular component of the molecular binding pair, a complex comprising the second molecular component labeled with the detection agent (labeled rFc-RBD), the neutralizing antibody, and the mouse anti-hIG is not formed, and thus no detectable signal or only a weakly detectable signal occurs at the second test line 410. The control line 412 comprises immobilized anti-rabbit IgG to capture labeled rFc-RBD that passes through the first test line 408 and second test line 410, thereby confirming proper operation of the test strip. In some embodiments, the test strip 400 is configured for quantification of the amount of the neutralizing antibody that blocks binding of the first molecular component and the second molecular component, e.g., based on the binding of the labeled second molecular component in the first test line 408.

Figure 5:
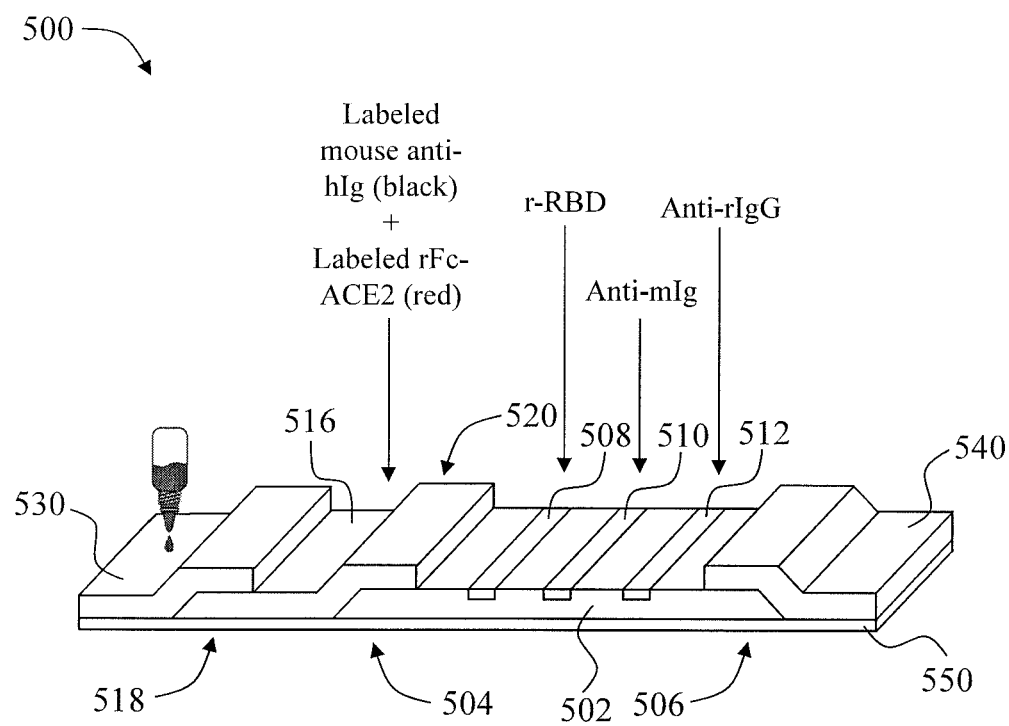
FIG. 5 shows a schematic of an exemplary test strip 500 comprising: (a) a chromatographic strip 502 comprising: (i) a first test line 508 comprising an immobilized recombinant RBD polypeptide (r-RBD), (ii) a first control line 510 comprising an immobilized anti-mouse Ig binding agent (anti-mIg), and (iii) a second control line 512 comprising an immobilized anti-rabbit IgG binding agent (anti-rIgG); and (b) a binding pad 516 comprising a rabbit Fc-ACE2 fusion polypeptide (rFc-ACE2) labeled with a first detection agent, and (ii) a mouse anti-human Ig binding agent (mouse anti-hIg) labeled with a second detection agent.

FIG. 5 shows an illustration of an exemplary test strip 500 for detection of a neutralizing antibody that blocks binding of a first molecular component and a second molecular component of a molecular binding pair, wherein the first molecular component comprises a recombinant receptor-binding domain polypeptide (r-RBD), and the second molecular component comprises a rabbit-Fc and ACE2 fusion polypeptide (rFc-ACE2). As shown in FIG. 5, the test strip 500 comprises a chromatographic strip 502 having a first end region 504 and a second end region 504, wherein the chromatographic strip 502 comprises a first test line 508, a first control line 510, and a second control line 512 positioned substantially perpendicular to the direction of fluid flow, wherein the first molecular component (r-RBD) is immobilized within the first test line 508, wherein an anti-mouse Ig binding agent is immobilized within the second test line 510, wherein an anti-rabbit IgG binding agent is immobilized within the second control line 512, and wherein the first test line 508, the second test line 510, and the second control line 512 are positioned in sequential order starting from the first end region 504 of the chromatographic strip 502. As shown in FIG. 5, the test strip comprises a sample binding zone comprising a binding pad 516 having a first end region 518 and a second end region 520, wherein the binding pad 516 comprises the red labeled second molecular component (a red labeled rFc-RBD) and the black labeled mouse anti-hIg binding agent. Additionally, the test strip illustrated in FIG. 5 comprises a sample addition zone comprising a sample pad 530, and an absorbent zone comprising a wicking pad 540. The illustrated test strip 500 also comprises a backing card 550 configured to support the other components of the test strip 500. The test strip 500 is configured such that the first end region 504 of the chromatographic strip 502 is in capillary communication with the second end region 520 of the binding pad 516, wherein the second end region 506 of the chromatographic strip 502 is in capillary communication with the wicking pad 540, and wherein the sample pad 530 is in capillary communication with the first end region 518 of the binding pad 516. In some embodiments, the recombinant RBD polypeptide is from a coronavirus. In some embodiments, the coronavirus is SARS-CoV-2 or SAR-CoV. In some embodiments, the ACE2 polypeptide is from human.

When the test strip 500 of FIG. 5 is in operation, a sample, or components thereof, travel via the sample pad 530 to the binding pad 516, and a fluid comprising the sample, or components thereof, the red labeled rFc-ACE2 fusion polypeptide, and the black labeled mouse anti-hIg enters the chromatographic strip 502. The fluid then travels via the chromatographic strip 502 from the first end region 504 to the second end region 506, including through the first test line 508, the first control line 510, and the second control line 512. In the presence of the neutralizing antibody that blocks binding of the first molecular component and the second molecular component of the molecular binding pair, the second molecular component labeled with the detection agent (the red labeled rFc-ACE2) is not bound by the immobilized first molecular component (r-RBD) in the first test line 510, and thus no detectable red signal or only a weakly detectable red signal occurs at the first test line 508. In the absence of the neutralizing that blocks binding of the first molecular component and the second molecular component of the molecular binding pair, the second molecular component labeled with the detection agent (red labeled rFc-ACE2) is bound by the immobilized first molecular component (r-RBD) in the first test line 508, and thus a detectable red signal occurs at the first test line 508. In the presence of an anti-RBD antibody in the sample, a complex comprising r-RBD immobilized at the first test line 508, the anti-RBD antibody, and black labeled mouse anti-hIg forms at the first test line 508, and thus a detectable black signal occurs at the first test line 508. The first control line 510 comprises immobilized anti-mouse IgG to capture the black labeled mouse anti-hIg (human IgG). The second control line 512 comprises immobilized anti-rabbit IgG to capture red labeled rFc (rabbit IgG Fc fragment)-ACE2 that passes through the first test line 508 and first control line 510, thereby confirming proper operation of the test strip. In some embodiments, the test strip 500 is configured for quantification of the amount of the neutralizing antibody that blocks binding of the first molecular component and the second molecular component, e.g., based on the binding of the labeled second molecular component in the first test line 508.

Figure 6:
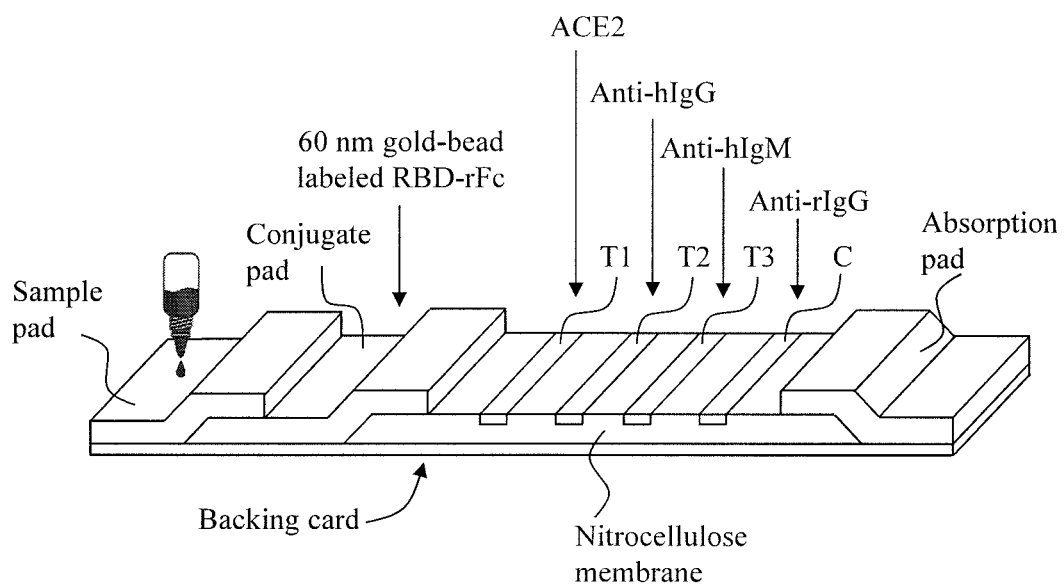
FIG. 6 shows a schematic of an exemplary test strip comprising: (a) a nitrocellulose membrane comprising: (i) a first test line comprising an immobilized ACE2 polypeptide (ACE), (ii) a second test line comprising an immobilized anti-human IgG binding agent (anti-hIgG), (iii) a third test line comprising an immobilized anti-human IgM binding agent (anti-hIgM), and (iv) a control line comprising an anti-rabbit IgG binding agent (anti-rIgG); (b) a binding pad comprising a 60 nm gold-bead (gold nanoparticle) labeled with RBD and a rabbit Fc tag; (c) a sample pad configured to accept the sample; and (d) an absorption pad.

FIG. 6 shows an illustration of an exemplary test strip for detection of a neutralizing antibody that blocks binding of a first molecular component and a second molecular component of a molecular binding pair, wherein the first molecular component comprises an ACE2 polypeptide (ACE2), and the second molecular component comprises a RBD polypeptide (RBD) conjugated to a gold bead and also having a rabbit-Fc. In some embodiments, the second molecular component and the rabbit-Fc are directly conjugated. In some embodiments, the second molecular component and the rabbit-Fc are connected via conjugation to the gold bead. As shown in FIG. 6, the test strip comprises a nitrocellulose membrane having a first end region and a second end region, wherein the nitrocellulose membrane comprises a first test line, a second test line, a third test line, and a control line positioned substantially perpendicular to the direction of fluid flow, wherein the first molecular component (ACE2) is immobilized within the first test line, wherein an anti-human IgG binding agent is immobilized within the second test line, wherein an anti-human IgM binding agent is immobilized within the third test line, wherein an anti-rabbit IgG binding agent is immobilized within the control line, and wherein the first test line, the second test line, the third test line, and the control line are positioned in sequential order starting from the first end region of the nitrocellulose membrane. As shown in FIG. 6, the test strip comprises a sample binding zone comprising a conjugate pad having a first end region and a second end region, wherein the conjugate pad 416 comprises the labeled second molecular component (a gold bead labeled with RBD and rabbit-Fc). Additionally, the test strip illustrated in FIG. 6 comprises a sample addition zone comprising a sample pad, and an absorbent zone comprising an absorption pad. The illustrated test strip also comprises a backing card configured to support the other components of the test strip. The test strip is configured such that the first end region of the nitrocellulose membrane is in capillary communication with the second end region of the conjugate pad, wherein the second end region of the nitrocellulose membrane is in capillary communication with the absorption pad, and wherein the sample pad is in capillary communication with the first end region of the conjugate pad. In some embodiments, the RBD polypeptide is from a coronavirus. In some embodiments, the coronavirus is SARS-CoV-2 or SAR-CoV. In some embodiments, the ACE2 polypeptide is from human. In some embodiments, the RBD polypeptide and/or ACE2 polypeptide are recombinant polypeptides.

When the test strip of FIG. 6 is in operation, a sample, or components thereof, travel via the sample pad to the conjugate pad, and a fluid comprising the sample, or components thereof, the gold bead labeled with a RBD polypeptide and a rFc enters the nitrocellulose strip. The fluid then travels via the nitrocellulose strip from the first end region to the second end region, including through the first test line, the second test line, the third test line, and the control line. In the presence of a neutralizing antibody that blocks binding of the first molecular component (ACE2) and the second molecular component (RBD) of the molecular binding pair, the second molecular component labeled with the detection agent (the gold bead labeled with a RBD polypeptide and a rFc) is not bound by the immobilized first molecular component (ACE2) in the first test line, and thus no detectable signal or only a weakly detectable signal occurs at the first test line. In the absence of a neutralizing antibody that blocks binding of the first molecular component and the second molecular component of the molecular binding pair, the second molecular component labeled with the detection agent (the gold bead labeled with a RBD polypeptide and a rFc) is bound by the immobilized first molecular component (ACE2) in the first test line, and thus a detectable signal occurs at the first test line. Additional signal configurations are presented in FIG. 6 based on the presence or absence of neutralizing antibodies, IgG, and IgM.

III. Devices

In some aspects, provided herein are devices comprising any test strip described herein. The devices encompassed in the present application facilitate use of the test strips by, e.g., holding a test strip in a specified manner, protecting the test strip, and aligning the test strip with features of the device such as for applying sample to the test strip and reading the results of the test strip. In some embodiments, the device comprises one test strip described herein. In some embodiments, the device comprises two or more test strips described herein.

In some embodiments, the device comprises one or more features facilitating the use of the test strip. For example, in some embodiments, the device comprises a sample port, wherein the sample port is configured to direct sample to a specific zone or component of the test strip, e.g., the sample addition zone, the sample pad, the sample binding zone, the binding pad, or the chromatographic strip. In some embodiments, the device comprises indicators to facilitate interpretation of the results of the test strip, e.g., markings to indicate test and control zones, a guide to read presence or absence of signal in a test or control zone. In some embodiments, the device comprises a feature to connect the device with an electronic device, e.g., for operation of the test strip and/or read-out of results from the test strip. In some embodiments, the device comprises a feature for the digital read-out of results of the test strip. In some embodiments, the device comprises a feature to establish communication to a mobile electronic device, computer, or mobile phone.

In some embodiments, the device is configured to use test strips as disposable components, e.g., a test strip may be placed in and removed from the device.

IV. Methods of Making and Using, Systems, and Kits

The present disclosure provides, in some aspects, methods of making and using the test strips disclosed herein, systems comprising the test strips disclosed herein and/or results therefrom, and kits comprising the test strips disclosed herein.

In some embodiments, provided herein is a method of making a test strip described herein. In some embodiments, the method comprises obtaining and assembling components of the test strip described herein. In some embodiments, provided herein is a method of making a device described herein.

In some embodiments, provided herein is a method of detecting the presence or absence of an analyte that blocks binding of a first molecular component and a second molecular component of a molecular binding pair, the method comprising: (a) introducing a sample from an individual to a device comprising any test strip described herein; and (b) analyzing one or more read-outs of the test strip, thereby detecting the presence or absence of the analyte in the sample from the individual. In some embodiments, the molecular binding pair comprises: (i) a viral-surface polypeptide or a fragment thereof and (ii) a cell-surface polypeptide or a fragment thereof. In some embodiments, the viral-surface polypeptide comprises a receptor-binding domain (RBD) of a spike protein from a virus. In some embodiments, the viral-surface polypeptide comprises a N-terminus domain (NTD) of a spike protein from a virus. In some embodiments, the virus is a coronavirus. In some embodiments, the coronavirus is SARS-CoV-2 or SAR-CoV. In some embodiments, the cell-surface polypeptide is ACE2. In some embodiments, the method further comprises quantifying the amount of the analyte present in the sample from the individual. In some embodiments, the sample is a whole blood or plasma sample. In some embodiments, the individual is a human.

In some embodiments, the method comprises obtaining the sample, such as a blood sample. In some embodiments, the method comprises obtaining the sample using a finger prick, such as a lancet finger prick. In some embodiments, the sample is diluted prior to application to a test device described herein. In some embodiments, the sample is diluted by a dilution factor of about 1:4 to about 1:20,000. In some embodiments, the sample dilution factor is at least about 1:4, such as at least about any of 1:8, 1:12, 1:16, 1:20, 1:40, 1:60, 1:80, 1:100, 1:500, or 1:1000. In some embodiments, the sample dilution factor is about 1:12. In some embodiments, the fluid containing the sample added to the test device is about 5 μL to about 500 μL. In some embodiments, the method comprises adding a buffer to the sample pad after the sample pad has been added, e.g., about 5 μL to about 500 μL of a buffer. In some embodiments, the buffer comprises PBS. In some embodiments, the buffer comprises PBS and EDTA.

In some embodiments, when using a test device described herein, a negative result (lack of the presence of a neutralizing antibody in a sample, can be identified from a single run using the test device. In some embodiments, to confirm a positive result (presence of a neutralizing antibody), an $IC_{50}$ is determined using more than one sample concentration. In some embodiments, when using a test device described herein, a positive or negative result is based on a cut-off value (e.g., the signal from the test device is above or below a cut-off value). For example, in some embodiments, the cut-off value is an average or median value of a set of control signals (such as obtained from a plurality of normal or healthy samples). In some embodiments, the cut-off value is an average or median value of a set of control signals plus at least about 1 standard deviation, such as at least about any of 1.5 standard deviations, 2 standard deviations, 2.5 standard deviations, 3 standard deviations, 3.5 standard deviations, 4 standard deviations, 4.5 standard deviations, or 5 standard deviations.

In some embodiments, provided herein is a testing system, including the individual components thereof. For example, in some embodiments, the system comprises a test device described herein and a computer device, such as a mobile phone, configured for imaging the test results and/or data processing. In some embodiments, the mobile phone comprises a camera. In some embodiments, the system comprises a web-based platform for data processing. In some embodiments, the data processing comprises converting the captured image to digital signal, such as by using ImageJ. In some embodiments, the data processing comprises converting the signal from the image of the test device, such as by calculating and/or graphing, e.g., by GraphPad Prisma 8 software.

In some embodiments, the method of using a test device described herein (from application of sample to test result) is completed within about 30 minutes, such as within about any of 25 minutes, 20 minutes, 15 minutes, 10 minutes, or 5 minutes. In some embodiments, the method of using a test device described herein is completed in 15 minutes or less.

In some embodiments, provided herein is a method of diagnosing an individual based on the presence or absence of an analyte that blocks binding of a first molecular component and a second molecular component of a molecular binding pair, the method comprising analyzing a sample from the individual using a test strip described herein, thereby diagnosing the individual based on the presence or absence of the analyte. In some embodiments, the analyte is a neutralizing antibody. In some embodiments, molecular binding pair comprises: (i) a viral-surface polypeptide or a fragment thereof; and (ii) a cell-surface polypeptide or a fragment thereof. In some embodiments, the viral-surface polypeptide comprises a receptor-binding domain (RBD) of a spike protein from a virus. In some embodiments, the viral-surface polypeptide comprises a N-terminus domain (NTD) of a spike protein from a virus. In some embodiments, the virus is a coronavirus. In some embodiments, the coronavirus is SARS-CoV-2 or SAR-CoV. In some embodiments, the cell-surface polypeptide is ACE2. In some embodiments, the method further comprises quantifying the amount of the analyte present in the sample from the individual. In some embodiments, the sample is a whole blood or plasma sample. In some embodiments, the individual is a human. In some embodiments, the method further comprises analyzing one or more additional characteristics of the individual, such as medical history, one or more symptoms, and temperature.

In some embodiments, provided herein is a method of treating an individual, the method comprising: (a) analyzing a sample from the individual using a test strip described herein; (b) administering a treatment to the individual based on the presence or absence of the analyte. In some embodiments, the analyte is a neutralizing antibody. In some embodiments, molecular binding pair comprises: (i) a viral-surface polypeptide or a fragment thereof; and (ii) a cell-surface polypeptide or a fragment thereof. In some embodiments, the viral-surface polypeptide comprises a receptor-binding domain (RBD) of a spike protein from a virus. In some embodiments, the viral-surface polypeptide comprises a N-terminus domain (NTD) of a spike protein from a virus. In some embodiments, the virus is a coronavirus. In some embodiments, the coronavirus is SARS-CoV-2 or SAR-CoV. In some embodiments, the cell-surface polypeptide is ACE2. In some embodiments, the method further comprises quantifying the amount of the analyte present in the sample from the individual. In some embodiments, the sample is a whole blood or plasma sample. In some embodiments, the individual is a human. In some embodiments, the method further comprises analyzing one or more additional characteristics of the individual, such as medical history, one or more symptoms, and temperature.

In some aspects, provided herein are uses of the devices, including test strips, and methods described herein for screening individuals. In some embodiments, the screen is to assess a status of a viral infection, such as a COVID-19 infection. In some embodiments, the screening techniques provided herein identify an individual immune to a viral infection, such as a coronavirus infection. In some embodiments, the screening techniques provided herein identify an at-risk of a viral infection, such as a coronavirus infection.

The present disclosure, in some aspects, provides systems comprising a test strip disclosed herein. For example, in some embodiments, the system comprises a test strip described herein and a computer or an electronic device for use of the test strip.

In some aspects, provided herein are kits comprising a test strip described herein. In some embodiments, the kit comprises a device and one or more test strips described herein. In some embodiments, the kit comprises instruction for using the test strip.

EXAMPLES

Example 1: Materials and Methods

Eighty COVID-19 patient plasma samples including 50 PCR positive and 30 PCR negative were purchased from iSpecimens (Lexington, Mass.). All plasma samples were incubated for half an hour in a 65° C. water-bath followed by a 5 minutes centrifuge. Supernatants were collected and 0.01% thimerosal was added as a preservative before aliquoting and storage. Twenty plasma samples collected between 2014 and 2016 before the COVID-19 pandemic were used as controls during this study.

60 nm gold nanoparticles (GNP) were purchased from SigmaAldrich (Cat NO. 742015). The conjugation started by centrifuging 10 ml of the GNP at 2000 g for 20 min. The pellet was suspended in 1 mL 25 mM borate buffer whose pH was adjusted to 8.5 by sodium hydroxide. The target protein, either recombinant SARS-CoV-2(2019-nCoV) Spike RBD-rFc Recombinant protein from Sino Biological Inc. (Cat NO.: 40592) or Spike/S1 protein (S1 subunit His tag) from Sino Biological (Cat NO.: 40591), was added into the GNP solution and stirred at 1000 rpm. After 1 hr of incubation at ambient temperature, 0.4 ml borate buffer containing 10% BSA was added into the GNP solution. The mixtures were incubated for another 1 hour at room temperature. The mixtures were then centrifuged at 2000 g for 20 min to discard unbound protein. The precipitate was re-suspended in 1 ml PBS containing 1% BSA and stored at 4° C.

Two types of strips were prepared. One type was 2-line strips designed for neutralization sensitivity tests, and the other type was 4-line strips designed for testing the plasma samples from patients. The 2-line strips contained alpaca anti-rabbit IgG (H+L) from Jackson ImmunoResearch (Code: 611-005-215) or Rabbit anti mouse FcY fragment specific from Jackson ImmunoResearch (Code: 315-005-046) at control line and ACE2 protein from Sino Biological Inc. (Cat NO.: 10108) at T1 line. For the 4-line strips, donkey anti-human IgM, Fc5µ from Jackson ImmunoResearch (Code: 709-005-073) and donkey anti human FcY from Jackson ImmunoResearch (Code: 709-005-098) were used at T3 and T2, respectively. All the capture protein or antibodies were mixed with 2% trehalose and 10% sucrose before being applied onto nitrocellulose membranes. The concentration of each capture antibody was tested and optimized prior to use.

An automated lateral flow reagent dispenser from Claremont Bio was used for applying antibodies to Whatman FF170HP membranes. The membranes were then dried at 40° C. for 1 hour, blocked with PBS-1% BSA for 5 min and dried again in a 40° C. oven for an hour. Then, 2 cm wide wick pad and sample pad were cut by a paper trimmer. The Biodot LM5000™ Lamination system was used to assemble the membrane, sample pad, and wick pad. Lastly, a Matrix 2360 programmable shear was used to cut the assembly into 0.5 cm wide strips. All the strips were refrigerated in a vacuum sealed bag for storage.

A half-strip format was used in most of LFT neutralization tests. A ninety-six well microtiter plate was used to hold testing solution and strips during the test. For each testing solution, 5 μL of plasma or testing sample was added to a mixture of 5 μL of GNP conjugated RBD or S1 recombinant protein and 50 μL of PBS buffer containing EDTA. Final dilution of the plasma was 1:12. The strips were then dipped into the solution and left for 15 minutes. The results were then recorded by a smartphone camera, converted to digital signals by Image J, and calculated and graphed by GraphPad Prisma 8 software. The tests were conducted in duplicates for the generation of IC50. A normal plasma was always included as a negative control in the test. The two monoclonal neutralizing antibodies used during the development of this test were from Sino Biological Inc. (Cat NO. 40592-R001 and 40592-MM57).

Recombinant SARS-CoV-2 S1, N and E proteins and S and N proteins from 4 common cold coronaviruses, all purchased from Sino Biological, were coated 25 μl/well onto black high binding ELISA 384-well plates (Greiner Bio-One) at a concentration of 0.25 μg/mL in 50 mM carbonate buffer, pH 9.6. Then the plates were incubated overnight at 4° C. After being washed 3 times by PBS-T, PBS containing 1% BSA were applied to each well as a blocker. After one hour blocking at room temperature, plasma samples were diluted by the blocker to 1:20, 1:200, 1:2 k, 1:20 k and 1:200 k, and were added and incubated for 1 hour at room temperature. After washing another three times, the plates were incubated with HRP-conjugated goat anti human IgG or IgM (Jackson ImmunoResearch) for another hour at room temperature. After washing five more times, Amplex Red (Thermo Fisher) was used to develop a fluorescent signal. Plates were read by Flexstation 2 (Molecular Devices).

This protocol was modified from the ELISA protocol above. The plates were coated with RBD-rFc at 0.25 μg/ml for o/n at 4° C. Mix 1 μg/ml of ACE2-mFc with serially diluted plasma (1:5, 20, 80, 400, 1600, 6400, 25600, 102400). They were then added to RBD-rFc coated plates and incubated for 1 h. Next a HRP labeled anti-mouse IgG with minimal cross-reactivity with human IgG was used to generate a detection signal.

For the pseudovirus assay, HEK-293 cells (35 mm dish) at approximately 85% confluence were transfected with hACE2 plasmid (Addgene plasmid #1786, 500 ng plasmid+ 10 ul 293fectin from Thermo fisher Cat #12347019) with 200 μl Opti-DMEM; 48 hours after transfection, cells were seeded into 384 well plates at 7500 cells/well/25 μl 10% FBS complete DMEM medium; Transfected HEK-293 cells were confirmed for expression of hACE2 by cytology— 95%-100% of transfected cells expression hACE2. Plasma was used at 1:5 serial dilution (final concentration: 1:5, 1:25, 1:75; 1:375, 1:1875, and 1:9375); SARS-CoV-2 S lenti Pseudo viruses (BPS Bioscience Cat #79942) were used at 500 viruses/well; Polybrene Transfection Reagent (Millipore) was used at final 1 μg/ml to help the virus infection; Diluted plasma (or neutralizing Ab used at final concentration: 5 μg/ml, 1 μg/ml, 0.2 μg/ml, 0.04 μg/ml, 0.08 μg/ml, and 0.016 μg/ml) and Pseudo viruses were mixed and incubated at RT for 30 minutes; Approximately 25 μl of plasma and Pseudo viruses mixtures were added to each well with hACE2 expressing cells (totally 50 μl) in triplicates for each condition; spin down the plate at 1500 g for 15 min to help virus infection; Incubate cells at 37° C. for 48 hours; detect luciferase activity using One-Step Luciferase Assay System (BPS Bioscience Cat #60690-1); approximately 50 μl of luciferase assay working solution (Component A+Component B) were added to each well (totally 100 μl volume); gently rock the plate for 15 minutes at RT and Spin down at 1000 g for 3 minutes; measure firefly luminescence using a luminometer (Thermo-Fisher Fluoroskan-FL).

The lateral flow strips were imaged by a mobile phone under even LED light illuminations. The images were downloaded and analyzed by ImageJ (National Institutes of Health, Bethesda, Md., USA). In brief, after image conversions, the rectangle region of interest (ROI) was selected and computed to obtain mean gray value. Adjacent background gray value on the same strip was subtracted. Stain intensity was then normalized to that of control to get percentage signal intensity.

Example 2: The Design and Use of a Lateral Flow Test for Detecting a SARS-CoV-2 Neutralizing Antibody Currently available neutralizing antibody tests (e.g., comprising use of live ACE2-expressing cells, live SARS-CoV-2, a pseudovirus, or ELISA) require hours to days to complete and must be performed in a well-equipped laboratory. As demonstrated herein, the rapid lateral flow assays taught in the instant application are capable of assaying for a neutralizing antibody from a patient sample in about 15 minutes or less and can be performed at the point-of-care.

The majority of SARS-CoV-2 vaccines aim to target SARS-CoV-2's spike (S) protein or the S protein's receptor binding domain (RBD) in order to induce neutralizing antibodies (NAbs) that block the interaction of RBD with its receptor angiotensin-converting enzyme 2 (ACE2) on host cells. Unlike other binding antibodies (BAbs), NAbs represent a type of humoral immunity capable of neutralizing or blocking viruses from entering host cells, which prevents them from reproducing and causing severe damage. NAbs are not equally developed among the COVID-19 convalescent patients and IgG antibodies specific to RBD developed in patients with mild COVID-19 have been observed to decay rapidly (half-life of approximately 36 days). Multiple COVID-19 re-infection cases have been reported. Evaluation of SARS-CoV-2 NAbs is critical for both better understanding of immunity to COVID-19 and monitoring levels of protective immunity, e.g., among the recipients of a COVID-19 vaccine.

Plasma samples from eighty patients was purchased from a Bio-Bank company. 50 of the patients were PCR positive for SARS-CoV-2 (named P1-P50), and 30 were PCR negative (N1-N30). Plasma samples from twenty normal patients (NP1-NP20) were randomly picked from an in-house collection dated between 2014 and 2016, which is well prior to the COVID-19 pandemic. The normal samples were used to establish negative baselines.

An ELISA assay was developed to evaluate all 100 plasma patient samples. Using the ELISA assay, IgG and IgM BAbs specific to the spike (S) protein, envelop (E) protein, and nucleocapsid (N) protein of SARS-CoV-2 were measured for in all 100 patient plasma samples, and Nabs were measured for in the 80 patient plasma samples having confirmed positive and negative SARS-CoV-2 status (P1-P50 and N1-N30). In line with previous findings in the art, data analyses revealed that positive antibody response rates to N and E proteins were far lower than the response rates to S protein, and no patient responded to N or E protein without raising IgG or IgM against S protein. Thus, for remaining studies reported herein, only the S protein was measured. Based on the relative sensitivity of the ELISA assay (80 patients' plasmas vs the 20 normal plasmas), signals above average plus 2SD (2 standard deviations) of that of the 20 normal plasmas at 1:200 dilution were chosen as the positive cutoff for both IgG and IgM antibodies.

Additionally a pseudovirus-based neutralization test was also developed using a commercially available pseudovirus and a one-step luciferase detection system. This assay takes days of cell culture work before and after ACE2 gene transfection to run.

A neutralizing antibody lateral flow test (NAb LFT) was developed and designed having three test lines and one control line, and using 60 nm Gold Nanoparticle (GNP)-conjugated RBD and a rabbit-Fc, rFc, to display a signal (FIG. 6). Immobilized ACE2 was in test line 1 (T1; FIG. 6) to capture GNP-conjugated RBD if the interaction between RBD and ACE2 was not completely blocked by neutralizing antibodies present in the plasma. Two additional test lines showing anti-S1 protein or anti-RBD IgG (T2) and IgM (T3) were included as a positive reading reference for a SARS-CoV-2 positive specimen.

Example 3: Test with NAb LFT Devices

Figure 7:
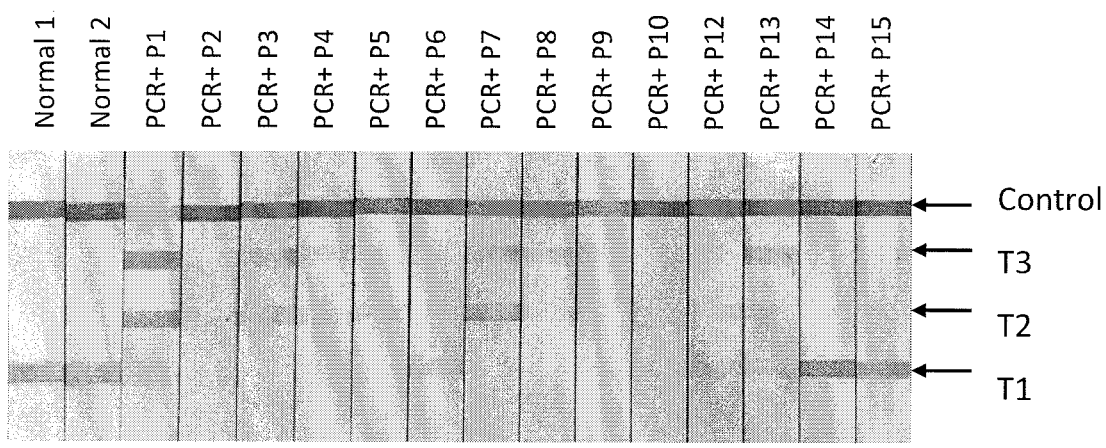
FIG. 7 shows results from exemplary test strips comprising three test lines and a control line.

Using NAb LFT devices, all patient plasma samples were assayed for NAbs. Each sample was analyzed using a separate NAb LFT device. To mimic the amount of sample typically obtained from use of a lancet finger prick, 10 µl of blood was taken and transferred to the sample pad of a NAb LFT device, and then 50-70 µl of buffer was added to drive the blood sample, and/or components thereof, through the NAb LFT device. The NAb LFT devices were then left until assay completion. A single dilution of 1:12 was used for the purpose to match the common practice in the field. Images of the NAb LFT devices after completing the assay were captured with a smartphone camera and analyzed with ImageJ software. The intensity of the test line was computed against that of a known negative plasma and presented as inhibition percentage. A good correlation was observed between the inhibition percentage at 1:12 dilution using the NAb LFT as compared to that obtained from the ELISA assay (r=0.79, 95% CI: 0.79-0.86, p<0.0001). Results of certain NAb LFT devices are provided in FIG. 7 (Control: negative control not having a neutralizing antibody; PCR+: PCR positive patient sample). As noted in FIG. 7, not all PCR positive patient samples contain neutralizing antibodies.

RT-PCR and PCR are currently considered as a gold standard in COVID-19 diagnosis and its result is often qualitatively presented as a positive or negative outcome. In order to compare the results from the NAb LFT devices with qualitative PCR results, it was demonstrated that all NAb LFT device quantitative results can be converted to a qualitative positive or negative outcome by using the cut-off established with the 20 normal plasma samples for S1 IgG and S1 IgM data and by using 50% inhibition at 1:12 dilution as the cut-off for NAb measurements. A very good negative percent agreement (90%) was observed between PCR and NAb LFT device inhibition assay results among PCR negative plasmas. 3 plasma samples that produced discordant results (negative PCR, but positive NAb LFT device) were repeatedly tested and found to contain neutralizing antibody by both inhibition ELISA and NAb LFT. It can be considered that these samples were false PCR negatives. In contrast, IgG and IgM against S1 protein showed very poor negative percent agreement with PCR and NAb LFT data. 53.3% of the 30 PCR negative patients showed S1 IgG and 66.7% showed S1 IgM. It is known that the S and N proteins among all seven human infecting coronaviruses share a significant amount of sequence homology and can induce cross reactive antibody responses. 21 To determine the contributing factor to these high negative percent disagreements, we tested 12 of the 30 PCR negative plasmas against S and N proteins of the 4 common cold coronaviruses, using the same ELISA protocol we used for SARS-CoV-2 proteins. Surprisingly, a higher IgG or IgM level against S or N proteins of at least one of the 4 common cold coronaviruses was observed, compared to that of SARS-CoV-2 among all 12 of the plasmas that were tested. Based on all of the available data, we believe that a certain percentage of PCR negative results were true false negatives and may be improved by testing patients' neutralizing antibody rather than their binding antibody. The possibility that some of the patients in this group actually suffered severe infection caused by one of the 4 common cold coronaviruses rather than by SARS-CoV-2 cannot ruled out.

Figure 8:
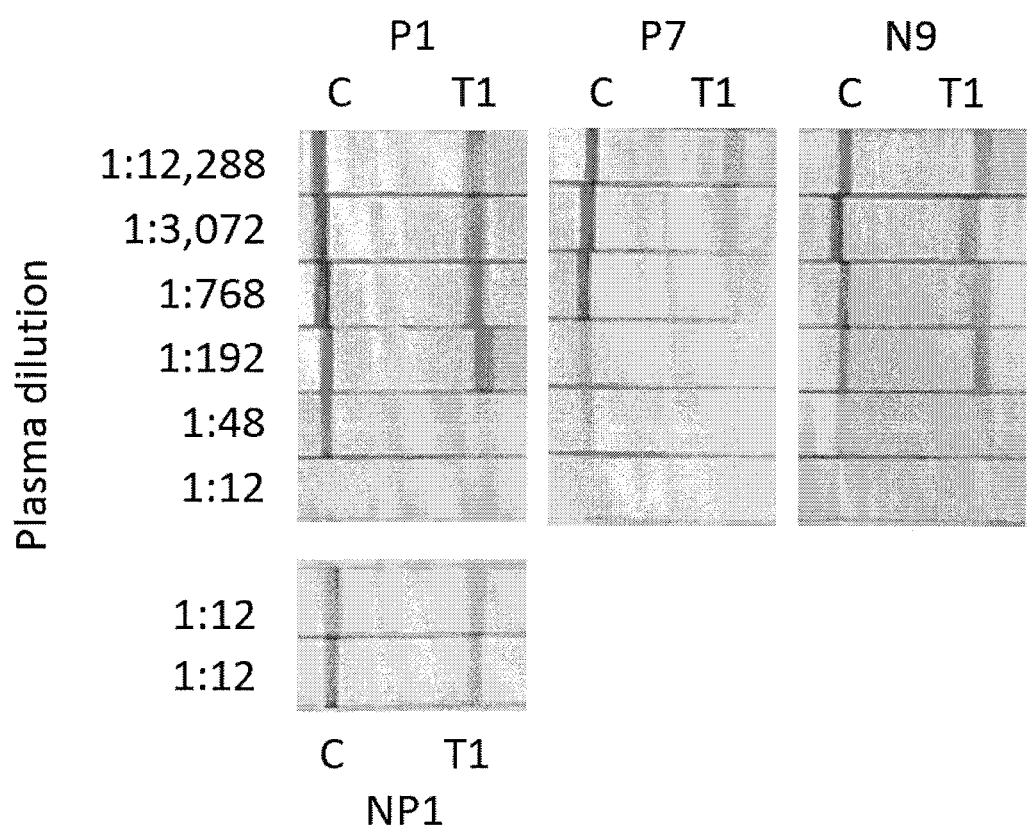
FIG. 8 shows results from exemplary test strips comprising a single test line and a control line run using a series of plasma dilutions.

Example 4: Test with NAb LFT Devices with a Positive Control (C) Line and T1 Line Using a NAb LFT device with a positive control (C) line and T1 line, IC50 measurement of two monoclonal NAbs and three plasmas were performed. A series of dilutions of each NAb or plasma were tested (FIG. 8). The results were computed with ImageJ software and then analyzed and graphed with GraphPad Prism. The same set of patients' plasmas were analyzed to compare this procedure with inhibition the ELISA and a pseudovirus neutralization assays. Comparable IC50 results were observed across the three tests. Among the three methods, the pseudovirus neutralization test is the most complicated, expensive and lengthy. Inhibition ELISA, while routine and a standard method in many laboratories, requires several hours of experimental work and needs to be performed in a laboratory setting. In contrast, the NAb LFT devices demonstrated above were completed within 15 minutes. In addition to the convenience and short turnaround time of the NAb LFT device, the NAb LFT device is highly flexible in its use and design. In other neutralization tests, a negative specimen needs to be tested for full dilution range in duplicate or triplicate in order to know the result. Using the NAb LFT device, all negative specimens were eliminated after testing a single concentration and then continuously testing specimens with a higher neutralizing antibody titer until IC50s was captured.

Example 5: Test with NAb LFT Devices for Mouse Neutralizing Antibodies

Figure 9A:
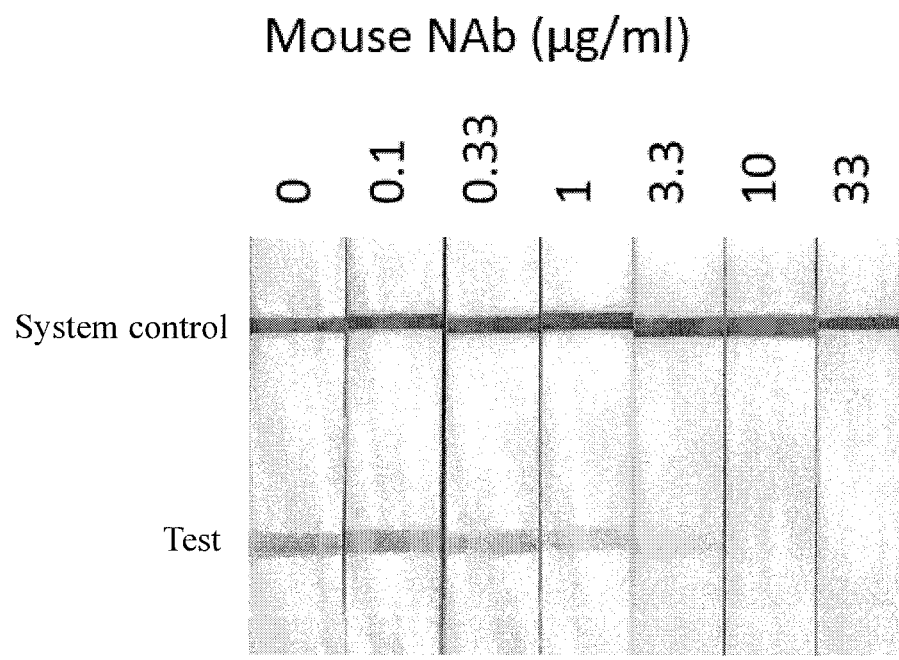
FIG. 9A shows exemplary test strips comprising a test line and a control line run using dilutions of a neutralizing antibody (NAb) in mouse plasma.
Figure 9B:
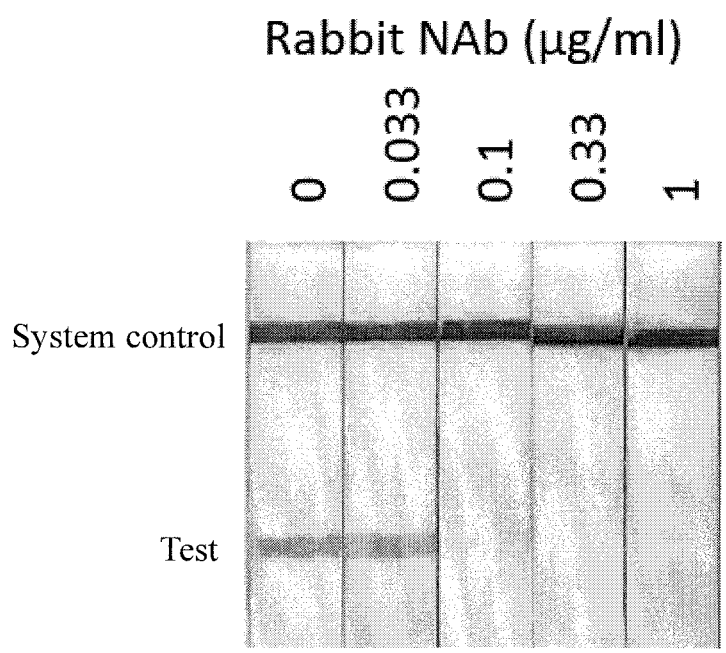
FIG. 9B show exemplary test strips comprising a test line and a control line run using dilutions of a neutralizing antibody (NAb) in rabbit plasma.

Similar dilution experiments were performed for mouse neutralizing antibodies (FIG. 9A) and rabbit neutralizing antibodies (FIG. 9B).

Any neutralization assays using live cell and live virus simultaneously measure neutralizing antibodies targeting three regions, N terminal domain (NTD) and RBD in S1 and cell fusion domain in S2. NAb LFT and ELISA are dependent on the protein fragment used, and can be used to evaluate NAbs specific to one or two domains in S1 protein. The performance of GNP labeled RBD with GNP labeled S1 was compared and a higher NAb titer was found by using GNP labeled S1. This higher NAb titer was not seen in the pseudovirus neutralization test.

Figure 10:
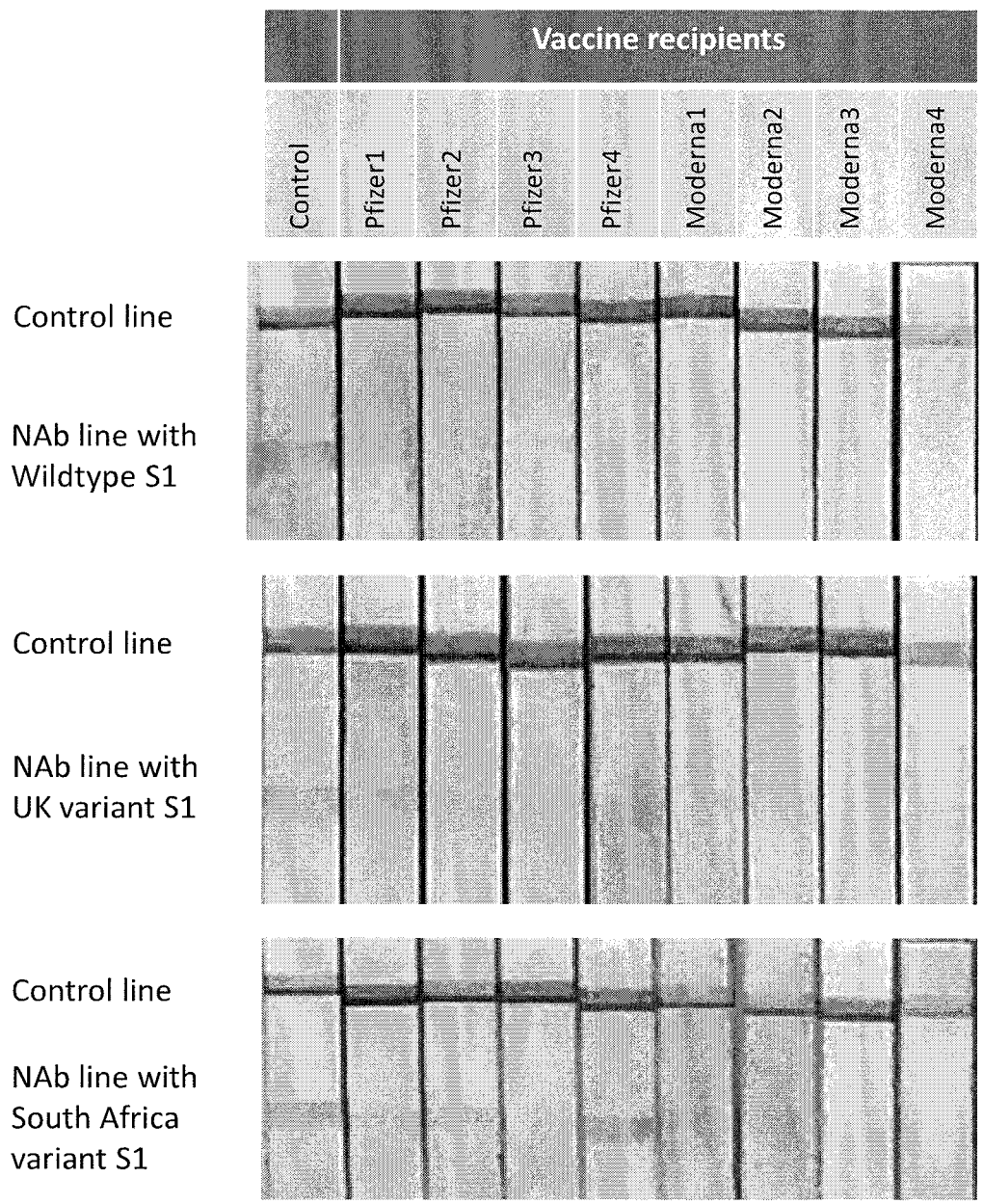
FIG. 10 shows exemplary test strips comprising a test line and a control line run using gold nanoparticle labeled spike protein from wild-type SARS-CoV-2 and two variants and plasmas from COVID-19 vaccine recipients.

Example 6: Test of NAb LFT Devices with Gold Nanoparticle Labeled SARS-CoV-2 Spike Proteins Using a NAb LFT device with a positive control (C) line and T1 line and GNP labeled S1 from wild-type and variants of SARS-CoV-2, inhibition sensitivity of the plasmas from COVID-19 vaccine recipients against different viral variants were demonstrated. The plasmas were collected 2-4 weeks after second dose of either Pfizer/BioNTech or Moderna vaccine. As shown in FIG. 10, all of the plasmas tested showed 100% or nearly 100% neutralization to wildtype and UK variant (B.1.1.7) and 50%-100% neutralization to South Africa variant (B1.351) with the NAb LFT device.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

What is claimed is:

1. A method of detecting the presence or absence of a neutralizing antibody that blocks binding of a first molecular component and a second molecular component of a molecular binding pair, the method comprising
    (a) introducing a sample from an individual to a test strip for detection of a neutralizing antibody that blocks binding of a first molecular component and a second molecular component of a molecular binding pair, wherein the first molecular component comprises a receptor-binding domain (RBD) and/or an N-terminal domain (NTD) of a spike protein from SARS-CoV-2, SARS-CoV, or a binding fragment thereof, and the second molecular component comprises an angiotensin-converting enzyme 2 (ACE2) or a binding fragment thereof, the second molecular component being fused to at least a portion of a non-human Fc region and labeled with a detection agent,
    wherein the test strip comprises:
        (i) a chromatographic strip having a first end region and a second end region, wherein the chromatographic strip comprises a first test line and a control line positioned substantially perpendicular to a direction of fluid flow, wherein the first molecular component is immobilized within the first test line, wherein an anti-non-human IgG binding agent is immobilized within the control line, and wherein the first test line is positioned closer to the first end region relative to the positioning of the control line;
        (ii) a sample binding pad having a first end region and a second end region, wherein second molecular component is pre-loaded within the sample binding pad, wherein the portion of the non-human Fc region is capable of binding the anti-non-human IgG binding agent;
        (iii) a sample addition pad; and
        (iv) an absorbent wicking pad,
    wherein the first end region of the chromatographic strip is in capillary communication with the second end region of the sample binding pad, wherein the second end region of the chromatographic strip is in capillary communication with the wicking pad, and wherein the sample addition pad is in capillary communication with the first end region of the sample binding pad; and
    (b) analyzing binding of a neutralizing antibody to the first test zone of the test strip,
    wherein an absence of binding of the second molecular component and an absence of a detectable signal in the first test line indicates the presence of the neutralizing antibody in the sample, and
    wherein a presence of binding of the second molecular component and a presence of a detectable signal in the first test line indicates the absence of the neutralizing antibody in the sample.

2. The method of claim 1, wherein the sample is a plasma sample.

3. The method of claim 1, wherein the molecular binding pair does not comprise an antibody or a fragment thereof.

4. The method of claim 1, wherein the sample is a plasma sample.

5. A method of detecting the presence or absence of a neutralizing antibody that blocks binding of a first molecular component and a second molecular component of a molecular binding pair, the method comprising:
    (a) introducing a sample from an individual to a test strip for detection of a neutralizing antibody that blocks binding of the first molecular component and the second molecular component, wherein the first molecular component comprises ACE2 or a binding fragment thereof, and the second molecular component comprises a RBD and/or NTD of a spike protein from BARS-CoV-2, BARS-CoV, or a binding fragment thereof, the second molecular component being fused to at least a portion of a non-human Fc region and labeled with a detection agent,
    wherein the test strip comprises:
        (i) a chromatographic strip having a first end region and a second end region, wherein the chromatographic strip comprises a first test line and a control line positioned substantially perpendicular to a direction of fluid flow, wherein the first molecular component is immobilized within the first test line, wherein an anti-non-human IgG binding agent is immobilized within the control line, and wherein the first test line is positioned closer to the first end region relative to the positioning of the control line;
        (ii) a sample binding pad having a first end region and a second end region, wherein the second molecular component is pre-loaded within the sample binding pad, wherein the portion of the non-human Fc region is capable binding the anti-non-human IgG binding agent;
        (iii) a sample addition pad; and
        (iv) an absorbent wicking pad,
    wherein the first end region of the chromatographic strip is in capillary communication with the second end region of the sample binding pad, wherein the second end region of the chromatographic strip is in capillary communication with the wicking pad, and wherein the sample addition pad is in capillary communication with the first end region of the sample binding pad; and
    (b) analyzing binding of a neutralizing antibody to one or more test zones of the test strip,
    wherein an absence of binding of the second molecular component and an absence of a detectable signal in the first test line indicates the presence of the neutralizing antibody in the sample, and
    wherein a presence of binding of the second molecular component and a presence of a detectable signal in the first test line indicates the absence of the neutralizing antibody in the sample.

6. The method of claim 5, wherein the molecular binding pair does not comprise an antibody or a fragment thereof.

* * * * *